United States Patent
Lindsley et al.

(10) Patent No.: US 12,319,701 B2
(45) Date of Patent: Jun. 3, 2025

(54) ANTAGONISTS OF THE MUSCARINIC ACETYLCHOLINE RECEPTOR M4

(71) Applicant: Vanderbilt University, Nashville, TN (US)

(72) Inventors: Craig W. Lindsley, Brentwood, TN (US); P. Jeffrey Conn, Nashville, TN (US); Aaron M. Bender, Spring Hill, TN (US); Matthew Spock, Nashville, TN (US); Changho Han, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 297 days.

(21) Appl. No.: 17/766,341

(22) PCT Filed: Oct. 2, 2020

(86) PCT No.: PCT/US2020/053942
§ 371 (c)(1),
(2) Date: Apr. 4, 2022

(87) PCT Pub. No.: WO2021/067696
PCT Pub. Date: Apr. 8, 2021

(65) Prior Publication Data
US 2024/0083907 A1    Mar. 14, 2024

Related U.S. Application Data

(60) Provisional application No. 62/910,863, filed on Oct. 4, 2019.

(51) Int. Cl.
*C07D 495/04* (2006.01)
*C07B 59/00* (2006.01)
*C07D 405/14* (2006.01)

(52) U.S. Cl.
CPC .......... *C07D 495/04* (2013.01); *C07B 59/002* (2013.01); *C07D 405/14* (2013.01); *C07B 2200/05* (2013.01)

(58) Field of Classification Search
None
See application file for complete search history.

(56) References Cited

U.S. PATENT DOCUMENTS

| | | |
|---|---|---|
| 7,560,551 B2 | 7/2009 | Cee et al. |
| 7,745,449 B2 | 6/2010 | Hong et al. |
| 8,691,865 B2 | 4/2014 | Searle et al. |
| 11,299,481 B2 | 4/2022 | Lindsley et al. |
| 11,820,757 B2 | 11/2023 | Lindsley et al. |
| 2021/0188820 A1 | 6/2021 | Lindsley et al. |
| 2022/0213069 A1 | 7/2022 | Lindsley et al. |
| 2023/0122344 A1 | 4/2023 | Lindsley et al. |
| 2023/0150986 A1 | 5/2023 | Lindsley et al. |
| 2023/0183218 A1 | 6/2023 | Lindsley et al. |
| 2023/0183219 A1 | 6/2023 | Lindsley et al. |

FOREIGN PATENT DOCUMENTS

| | | |
|---|---|---|
| WO | 2007087276 A1 | 8/2007 |
| WO | 2015027204 A1 | 2/2015 |
| WO | 2017143041 A1 | 8/2017 |
| WO | 2018042362 A1 | 3/2018 |
| WO | 2019079783 A1 | 4/2019 |
| WO | 2019089676 A1 | 5/2019 |
| WO | 2019152809 A1 | 8/2019 |
| WO | 2021119254 A1 | 6/2021 |
| WO | 2021119265 A1 | 6/2021 |
| WO | 2021216949 A1 | 10/2021 |
| WO | 2021216951 A1 | 10/2021 |
| WO | 2022109099 A1 | 5/2022 |
| WO | 2022140499 A1 | 6/2022 |
| WO | 2022212819 A1 | 10/2022 |
| WO | 2022216655 A1 | 10/2022 |
| WO | 2022261427 A1 | 12/2022 |
| WO | 2023102100 A1 | 6/2023 |

OTHER PUBLICATIONS

European Patent Office Extended European Search Report for application 20873262.8, dated Mar. 31, 2023 (9 pages).
International Preliminary Report on Patentability for Application No. PCT/US2020/053942 dated Apr. 5, 2022 (6 pages).
International Search Report and Written Opinion for Application No. PCT/US2020/053942 dated Jan. 8, 2021 (12 pages).
Tsuji, T. et al. "Discovery of novel pyridazine derivatives as glucose transporter type 4 (GLUT4) translocation activators." Bioorganic & Medicinal Chemistry Letters 29.14 (2019): 1785-1790.
Wood, M. R., et al. "Discovery and optimization of a novel series of highly CNS penetrant M4 PAMs based on a 5, 6-dimethyl-4-(piperidin-1-yl) thieno [2, 3-d] pyrimidine core." Bioorganic & medicinal chemistry letters 26.13 (2016): 3029-3033.

*Primary Examiner* — Zinna Northington Davis
(74) *Attorney, Agent, or Firm* — COOLEY LLP

(57) ABSTRACT

Disclosed herein are substituted hexahydro-1H-cyclopenta [c]pyrrole compounds, which may be useful as antagonists of the muscarinic acetylcholine receptor $M_4$ (mAChR $M_4$). Also disclosed herein are methods of making the compounds, pharmaceutical compositions comprising the compounds, and methods of treating disorders using the compounds and compositions.

20 Claims, No Drawings

ANTAGONISTS OF THE MUSCARINIC ACETYLCHOLINE RECEPTOR M4

RELATED APPLICATIONS

This patent application is the U.S. national stage entry, under 35 U.S.C. § 371, of International Application Number PCT/US2020/053942, filed Oct. 2, 2020, which claims priority to U.S. Provisional Application No. 62/910,863, filed Oct. 4, 2019, the entire contents of each of which are hereby incorporated by reference.

STATEMENT OF GOVERNMENT INTEREST

This invention was made with government support under Grant Number W81XWH-19-1-0355, awarded by the Department of Defense. The Government has certain rights in the invention.

TECHNICAL FIELD

The present disclosure relates to compounds, compositions, and methods for treating disorders associated with muscarinic acetylcholine receptor dysfunction.

BACKGROUND

Parkinson's disease (PD) is the second most common neurodegenerative disease with an increasing prevalence as a function of age. Moreover, early-onset PD is also increasing. A hallmark of PD is the progressive degeneration and loss of dopaminergic neurons in the substantia nigra (SN) and basal ganglia (BG), leading to pronounced motor symptoms including bradykinesia, tremor, rigidity, gait dysfunction and postural instability. At present, levodopa (L-DOPA) is the standard of care for treating the motor symptoms, but it is not curative, and prolonged use can engender L-DOPA induced dyskinesia (LID).

Prior to L-DOPA, compounds with anticholinergic activity represented the preferred mode of PD treatment. Cholinergic neurons provide important neuromodulatory control of the BG motor circuit. While the actions of cholinergic pathways on basal ganglia pathways are complex, activation of muscarinic acetylcholine receptors (mAChRs) generally have actions that oppose dopamine (DA) signaling. For instance, mAChR agonists inhibit DA release, and inhibit multiple behavioral effects of drugs that increase DA levels and signaling. Interestingly, muscarinic acetylcholine receptor (mAChR) antagonists were the first available treatments for PD and are still widely used for treatment of this disorder. While many studies of the actions of mAChR antagonists were carried out before randomized controlled trials were introduced, recent well controlled double-blind cross-over design studies demonstrate significant improvement in multiple aspects of motor function in patients receiving mAChR antagonists. Unfortunately, mAChR antagonists have a number of dose-limiting adverse effects that severely limit their clinical utility, including multiple peripheral adverse effects, as well as confusion and severe cognitive disturbances.

Because adverse effects associated with mAChR antagonists limit the doses that can be tolerated, previous clinical studies may underestimate the efficacy that could be achieved if doses of mAChR antagonists could be increased to achieve more complete blockade of specific mAChR subtypes responsible for the antiparkinsonian effects of these agents. The mAChRs include five subtypes, termed $M_1$-$M_5$. Available mAChR antagonists, such as scopolamine, are nonselective across these subtypes, and many of their adverse effects are likely mediated by mAChR subtypes that are not involved in the antiparkinsonian activity. Thus, compounds possessing a more selective profile for individual mAChRs may offer an advantage in PD, as well as related disorders such as dystonia. For example, some studies indicate that the $M_4$ mAChR subtype may play a dominant role in mAChR regulation of basal ganglia motor function.

SUMMARY

In one aspect, disclosed are compounds of formula (I),

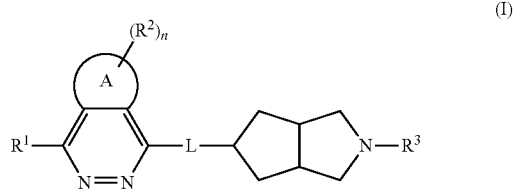

or a pharmaceutically acceptable salt thereof, wherein:
A is a 5- to 6-membered heteroarene, a 5- to 6-membered heterocycle, a 6-membered arene, or a 5- to 6-membered carbocycle, the heteroarene and heterocycle having 1, 2, or 3 heteroatoms independently selected from N, O, and S;
L is NR or O;
R is hydrogen, $C_{1-4}$alkyl, $C_{3-4}$cycloalkyl, or —$C_{1-3}$alkylene—$C_{3-4}$cycloalkyl;
$R^1$ is $G^1$, —L'—$G^1$, —L'—$C_{1-3}$alkylene—$G^1$, hydrogen, $C_{1-6}$alkyl, $C_{1-6}$haloalkyl, —L'—$C_{1-6}$alkyl, —L'—$C_{1-6}$haloalkyl, —C(O)NH$_2$, or halogen;
L' is O, —N($R^{1a}$)—, S, S(O), SO$_2$, —C(O)—, or —N($R^{1a}$)C(O)—;
$G^1$ is a 6- to 12-membered aryl, a 5- to 12-membered heteroaryl, a 4- to 12-membered heterocyclyl, or a $C_{3-12}$carbocyclyl, wherein $G^1$ is optionally substituted with 1-5 substituents independently selected from the group consisting of halogen, cyano, $C_{1-4}$alkyl, $C_{1-4}$haloalkyl, —OR$^{10}$, —N(R$^{10}$)$_2$, —NR$^{10}$C(O)R$^{10}$, —CONR$^{10}$R$^{10}$, —NR$^{10}$SO$_2$R$^{11}$, $C_{1-3}$alkylene—OR$^{10}$, $C_{3-6}$cycloalkyl, and —$C_{1-3}$alkylene—$C_{3-6}$cycloalkyl;
$R^{1a}$ is hydrogen, $C_{1-4}$alkyl, $C_{1-4}$haloalkyl, $C_{3-4}$cycloalkyl, or —$C_{1-3}$alkylene—$C_{3-4}$cycloalkyl;
$R^{10}$, at each occurrence, is independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two $R^{10}$, together with a nitrogen to which the two $R^{10}$ attach form a 4- to 6-membered heterocyclic ring optionally substituted with 1-4 substituents independently selected from the group consisting of halogen and $C_{1-4}$alkyl;
$R^{11}$ is $C_{1-4}$alkyl, $C_{1-4}$haloalkyl, $C_{3-4}$cycloalkyl, or —$C_{1-3}$alkylene—$C_{3-4}$cycloalkyl;
$R^2$, at each occurrence, is independently halogen, cyano, $C_{1-4}$alkyl, $C_{1-4}$haloalkyl, $C_{2-4}$alkenyl, $C_{3-6}$cycloalkyl, or —$C_{1-3}$alkylene—$C_{3-4}$cycloalkyl;
n is 0, 1, 2, 3 or 4;
$R^3$ is $G^2$, —$L^1$—$G^2$, —$L^2$—$G^2$, —$C_{2-6}$alkylene—$R^{3a}$, or $C_{3-7}$alkyl;
$L^1$ is $C_{1-3}$alkylene;
$L^2$ is 1,1-cyclopropylene;

G² is a 6- to 12-membered aryl, a 5- to 12-membered heteroaryl, a 4- to 12-membered heterocyclyl, or a $C_{3-12}$carbocyclyl optionally fused to a 6-membered arene, wherein G² is optionally substituted with 1-5 substituents independently selected from the group consisting of halogen, cyano, $C_{1-4}$alkyl, $C_{1-4}$haloalkyl, —OR¹³, —N(R¹³)₂, —$C_{1-3}$alkylene—OR¹³, or —$C_{1-3}$alkylene—N(R¹³)₂;

R³ᵃ is —OR¹⁴ or —N(R¹⁴)₂; and

R¹³ and R¹⁴, at each occurrence, are independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two R¹³ or two R¹⁴, together with a nitrogen to which the two R¹³ or two R¹⁴ attach form a 4- to 6-membered heterocyclic ring optionally substituted with 1-4 substituents independently selected from the group consisting of halogen and $C_{1-4}$alkyl.

In another aspect, the invention provides a pharmaceutical composition comprising a compound of formula (I), or a pharmaceutically acceptable salt thereof, and a pharmaceutically acceptable carrier.

In another aspect, the invention provides a method of treating a disorder in a subject, wherein the subject would benefit from antagonism of mAChR M₄, comprising administering to the subject a therapeutically effective amount of a compound of formula (I), or a pharmaceutically acceptable salt or composition thereof.

In another aspect, the invention provides a method for antagonizing mAChR M₄ in a subject, comprising administering to the subject a therapeutically effective amount of a compound of formula (I), or a pharmaceutically acceptable salt or composition thereof.

In another aspect, the invention provides a method for the treatment of a neurodegenerative disorder, a movement disorder, or a brain disorder comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of a neurodegenerative disorder, a movement disorder, or a brain disorder.

In another aspect, the invention provides a compound of formula (I), or a pharmaceutically acceptable salt or composition thereof, for use in antagonizing mAChR M₄ in a subject.

In another aspect, the invention provides the use of a compound of formula (I), or a pharmaceutically acceptable salt or composition thereof, in the manufacture of a medicament for the treatment of a neurodegenerative disorder, a movement disorder, or a brain disorder.

In another aspect, the invention provides the use of a compound of formula (I), or a pharmaceutically acceptable salt or composition thereof, in the manufacture of a medicament for antagonizing mAChR M₄ in a subject.

In another aspect, the invention provides a kit comprising a compound of formula (I), or a pharmaceutically acceptable salt or composition thereof, and instructions for use.

DETAILED DESCRIPTION

Disclosed herein are compounds that are antagonists of the muscarinic acetylcholine receptor M₄ (mAChR M₄), methods of making the compounds, pharmaceutical compositions comprising the compounds, and methods of treating disorders using the compounds and pharmaceutical compositions. The compounds include substituted hexahydro-1H-cyclopenta[c]pyrrole compounds.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to a group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon, for example, of 1 to 3 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl.

The term "aryl," as used herein, refers to a phenyl or a phenyl appended to the parent molecular moiety and fused to a cycloalkyl group (e.g., indanyl), fused to an arene group (e.g., the aryl is naphthyl), or fused to a non-aromatic heterocycle (e.g., benzo[d][1,3]dioxol-5-yl). The term "phenyl" is used when referring to a substituent and the term 6-membered arene is used when referring to a fused ring. The 6-membered arene is monocyclic (e.g., benzene or benzo).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkane," as used herein, refers to a saturated ring system containing all carbon atoms as ring members and zero double bonds. The term "cycloalkyl" is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1] heptanyl), or a spirocycle. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1] pentanyl.

The term "cycloalkene," as used herein, means a non-aromatic monocyclic or multicyclic ring system containing all carbon atoms as ring members and at least one carbon-carbon double bond and preferably having from 5-10 carbon atoms per ring. The term "cycloalkenyl" is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1] heptenyl). Exemplary monocyclic cycloalkenyl rings include cyclopentenyl, cyclohexenyl or cycloheptenyl.

The term "carbocyclyl" means a "cycloalkyl" or a "cycloalkenyl."

The term "1,1-carbocyclylene" means a geminal divalent group derived from a cycloalkyl. A representative example is 1,1—C$_{3-6}$cycloalkylene (i.e.,

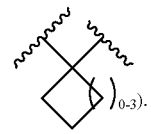

A further example is 1,1-cyclopropylene (i.e.,

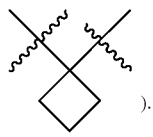 [SMILES: *C1(*)CCC1]

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The term "heteroaryl" is used herein to refer to a heteroarene when present as a substituent. The monocyclic heteroaryl are five or six membered rings containing at least one heteroatom independently selected from the group consisting of N, O, and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl is an 8- to 12-membered ring system having a monocyclic heteroaryl ring fused to a 6-membered arene (e.g., quinolinyl), fused to a monocyclic carbocyclic ring (e.g., 6,7-dihydro-5H-cyclopenta[b]pyridinyl), fused to a monocyclic heteroarene (e.g., naphthyridinyl), or fused to a monocyclic heterocycle (e.g., 2,3-dihydrofuro[3,2-b]pyridinyl). A bicyclic heteroaryl/heteroarene group includes a 9-membered fused bicyclic aromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl (e.g., thiazol-4-yl), 1,2,4-thiadiazolyl, 1,3,4-oxadiazolyl, 1,2,4-oxadiazolyl, imidazolyl, thiazolyl, isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), [1,2,4]triazolo[4,3-b]pyridazinyl (e.g., [1,2,4]triazolo[4,3-b]pyridazin-6-yl), naphthyridinyl, pyridoimidazolyl, thiazolo[5,4-b]pyridin-2-yl, thiazolo[5,4-d]pyrimidin-2-yl, and pyrrolo[2,3-c]pyridazin-3-yl.

The term "heterocycle" or "heterocyclic," as used herein, means a monocyclic heterocycle or a bicyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, or two double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-oxaspiro[3.3]heptan-6-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl) azabicyclo[3.1.0]hexanyl (including 3-azabicyclo[3.1.0]hexan-3-yl), 2,3-dihydro-1H-indol-1-yl, isoindolin-2-yl, and octahydrocyclopenta[c]pyrrolyl.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "mAChR $M_4$ receptor antagonist" as used herein refers to any exogenously administered compound or agent that directly or indirectly antagonizes mAChR $M_4$, for example in an animal, in particular a mammal (e.g., a human).

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, the invention provides compounds of formula (I), wherein A, L, $R^1$, $R^2$, $R^3$, and n are as defined herein.

In compounds of formula (I), ring A may be a 5-membered heteroarene, optionally substituted as defined herein. The 5-membered heteroarene may be a thiophene. In the compounds wherein ring A is the 5-membered heteroarene, n may be 0. Compounds of formula (I) may have formula (I-A)

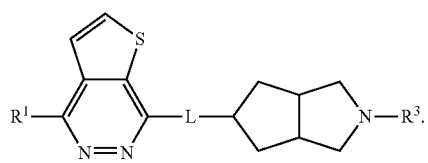

(I-A)

Compounds of formula (I) may have formula (I-B)

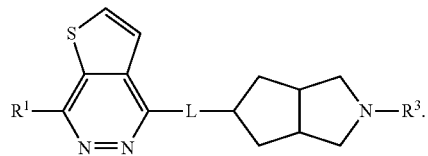

(I-B)

In compounds of formula (I), ring A may be a 6-membered arene, optionally substituted as defined herein. In the compounds wherein ring A is the 6-membered arene, n may be 0. Compounds of formula (I) may have formula (I-C)

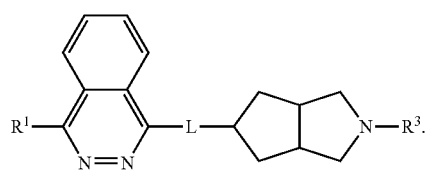

(I-C)

In compounds of formula (I), ring A may be a 6-membered carbocycle, optionally substituted as defined herein. The 6-membered carbocycle may be a 6-membered cycloalkane. In the compounds wherein ring A is the 6-membered carbocycle, n may be 0. Compounds of formula (I) may have formula (I-D)

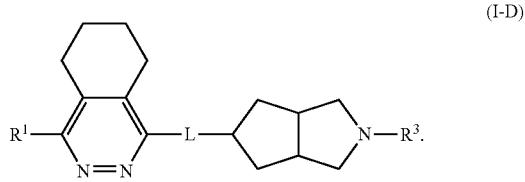

(I-D)

In compounds of formula (I), $R^1$ may be halogen (e.g., chloro).

In compounds of formula (I), $R^1$ may be $G^1$.

In the compounds of formula (I), $G^1$ may be a 6- to 12-membered aryl, optionally substituted as defined herein. The optionally substituted 6- to 12-membered aryl may be an optionally substituted phenyl. For example, the optionally substituted 6- to 12-membered aryl may be phenyl,

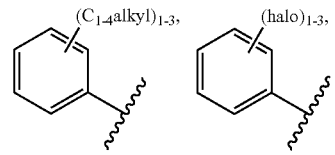

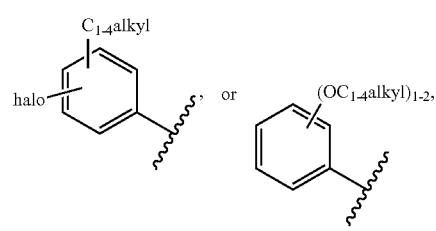

such as phenyl,

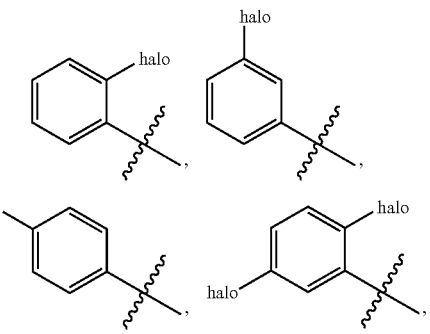

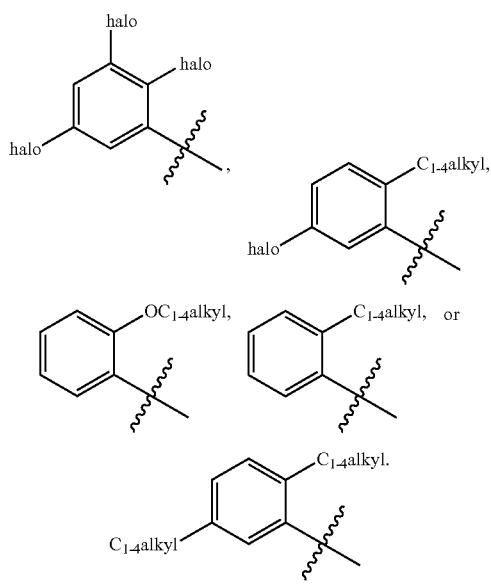

The halo in the optionally substituted phenyl may be fluoro or chloro and the $C_{1-4}$alkyl may be a methyl. The optionally substituted phenyl may be phenyl,

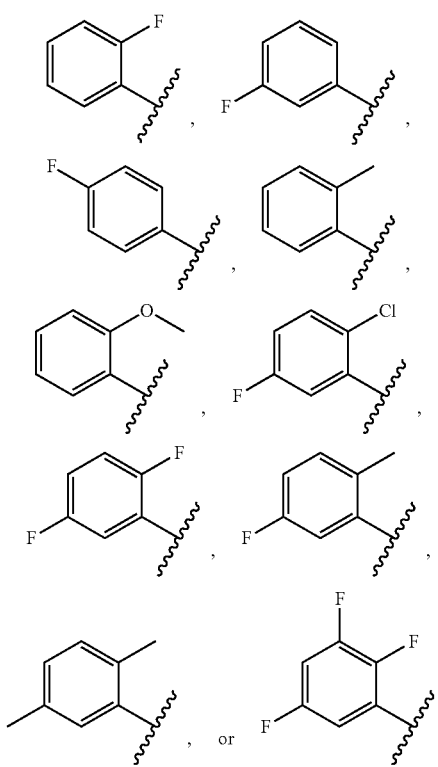

In the compounds of formula (I), $G^1$ may be a 5- to 12-membered heteroaryl, optionally substituted as defined herein. The optionally substituted 5- to 12-membered heteroaryl may be an optionally substituted indazolyl. For example, the optionally substituted indazolyl may be

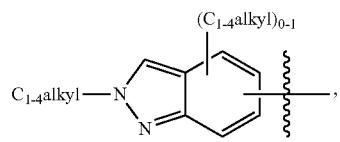

such as

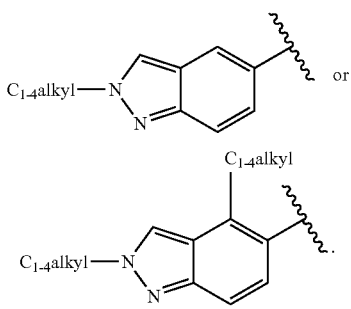

The $C_{1-4}$alkyl in the optionally substituted indazolyl may be a methyl. The optionally substituted indazolyl may be

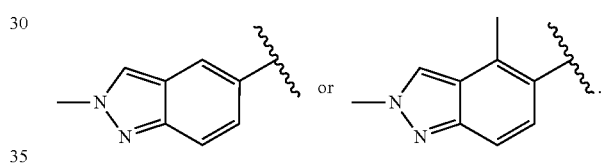

In the compounds of formula (I), $G^1$ may be a 4- to 12-membered heterocyclyl, optionally substituted as defined herein. The optionally substituted 4- to 12 membered heterocyclyl may be an optionally substituted 4- to 8-membered monocyclic heterocyclyl containing 1-2 heteroatoms independently selected from the group consisting of N and O. The optionally substituted heterocyclyl may be attached to the parent molecular moiety at a ring nitrogen atom of the heterocycicyl. For example, the optionally substituted 4- to 8-membered monocyclic heterocyclyl may be

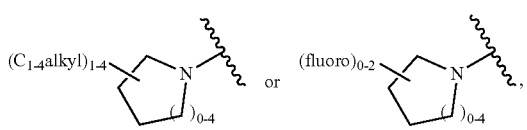

such as

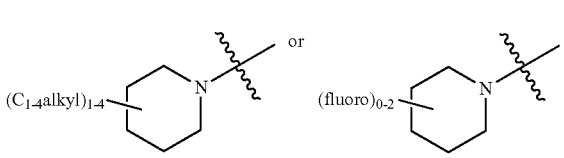

The $C_{1-4}$alkyl in the optionally substituted heterocyclyl may be a methyl. The optionally substituted heterocyclyl may be

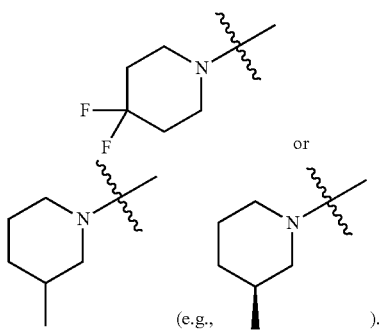

(e.g., 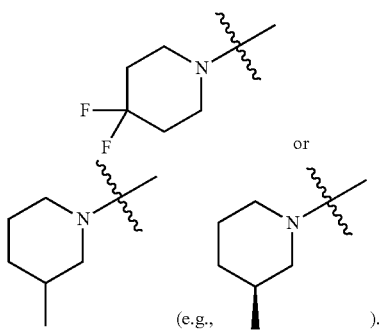).

In compounds of formula (I), L may be NR, such as formulas (I-A1), (I-B1), (I-C1), and (I-D1).

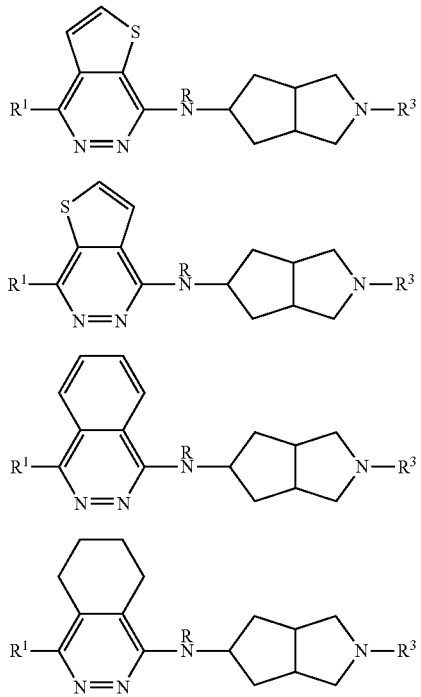

(I-A1)

(I-B1)

(I-C1)

(I-D1)

In compounds of formula (I), (I-A), (I-B), (I-C), (I-D), (I-A1), (I-B1), (I-C1), and (I-D1), R may be hydrogen.

In compounds of formula (I), L may be O.

In formula (I) and according to the embodiments herein, $R^3$ may be —$L^1$—$G^2$, wherein $L^1$ is as defined herein, and $G^2$ is an optionally substituted 4- to 12-membered heterocyclyl. The optionally substituted 4- to 12-membered heterocyclyl may be an optionally substituted 4- to 8-membered monocyclic heterocyclyl or a 7- to 12-membered spiro heterocyclyl, wherein the heterocyclyls contain one heteroatom selected from O and S. The optionally substituted 4- to 12-membered heterocyclyl may be an optionally substituted oxetanyl, tetrahydropyranyl, tetrahydrothiopyranyl, 2-oxaspiro[3.3]heptanyl, or 3-oxaspiro[5.5]undecanyl. The optionally substituted 4- to 12-membered heterocyclyl may be an optionally substituted 4- to 8-membered monocyclic heterocyclyl containing one oxygen atom. The optionally substituted 4- to 8-membered monocyclic heterocyclyl may be an optionally substituted tetrahydropyranyl. The optionally substituted 4- to 8-membered monocyclic heterocyclyl may be

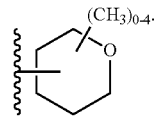

The optionally substituted 4- to 8-membered monocyclic heterocyclyl may be

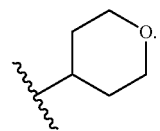 [SMILES: *C1CCOCC1]

In formula (I) and according to the embodiments herein, $R^3$ may be —$L^1$—$G^2$, wherein $G^2$ is as defined herein, and $L^1$ is $CH_2$.

Throughout the embodiments and description of the compounds of the invention, all instances of haloalkyl may be fluoroalkyl (e.g., any $C_{1-4}$haloalkyl may be $C_{1-4}$fluoroalkyl).

Representative compounds of formula (I) include, but are not limited to:

7-chloro-N-((3aR,5s,6aS)-2-((tetrahydro-2H-pyran-4-yl) methyl)octahydrocyclopenta[c]pyrrol-5-yl)thieno[2,3-d] pyridazin-4-amine;

7-(2,5-difluorophenyl)-N-((3aR,5s,6aS)-2-((tetrahydro-2H-pyran-4-yl) methyl)octahydrocyclopenta[c]pyrrol-5-yl) thieno[2,3-d]pyridazin-4-amine;

7-(5-fluoro-2-methylphenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-(2,5-dimethylphenyl)-N-((3aR,5s,6aS)-2-((tetrahydro-2H-pyran-4-yl) methyl)octahydrocyclopenta[c]pyrrol-5-yl) thieno[2,3-d]pyridazin-4-amine;

N-((3aR,5s,6aS)-2-((tetrahydro-2H-pyran-4-yl)methyl) octahydrocyclopenta[c]pyrrol-5-yl)-7-(o-tolyl)thieno[2,3-d] pyridazin-4-amine;

7-(2-methoxyphenyl)-N-((3aR,5s,6aS)-2-((tetrahydro-2H-pyran-4-yl) methyl)octahydrocyclopenta[c]pyrrol-5-yl) thieno[2,3-d]pyridazin-4-amine;

7-(2-fluorophenyl)-N-((3aR,5s,6aS)-2-((tetrahydro-2H-pyran-4-yl) methyl)octahydrocyclopenta[c]pyrrol-5-yl) thieno[2,3-d]pyridazin-4-amine;

7-phenyl-N-((3aR,5s,6aS)-2-((tetrahydro-2H-pyran-4-yl) methyl)octahydrocyclopenta[c]pyrrol-5-yl)thieno[2,3-d] pyridazin-4-amine;

7-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

4-(2,5-difluorophenyl)-N-((3aR,5s,6aS)-2-((tetrahydro-2H-pyran-4-yl) methyl)octahydrocyclopenta[c]pyrrol-5-yl) thieno[2,3-d]pyridazin-7-amine;

4-(5-fluoro-2-methylphenyl)-N-((3aR,5s,6aS)-2-((tetrahydro-2H-pyran-4-yl) methyl)octahydrocyclopenta[c]pyrrol-5-yl)thieno[2,3-d]pyridazin-7-amine;

4-chloro-N-((3aR,5s,6aS)-2-((tetrahydro-2H-pyran-4-yl) methyl)octahydrocyclopenta[c]pyrrol-5-yl)thieno[2,3-d] pyridazin-7-amine;

4-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-7-amine;

4-phenyl-N-((3aR,5s,6aS)-2-((tetrahydro-2H-pyran-4-yl) methyl)octahydrocyclopenta[c]pyrrol-5-yl)thieno[2,3-d]pyridazin-7-amine;

4-(2-fluorophenyl)-N-((3aR,5s,6aS)-2-((tetrahydro-2H-pyran-4-yl) methyl)octahydrocyclopenta[c]pyrrol-5-yl) thieno[2,3-d]pyridazin-7-amine;

N-((3aR,5s,6aS)-2-((tetrahydro-2H-pyran-4-yl)methyl) octahydrocyclopenta[c]pyrrol-5-y1)-7-(2,3,5-trifluorophenyl)thieno[2,3-d]pyridazin-4-amine;

7-(2,4-dimethyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

7-(2,5-difluorophenyl)-N-((3aR,5s,6aS)-2-((tetrahydro-2H-pyran-4-yl)methyl-d2) octahydrocyclopenta[c]pyrrol-5-yl)thieno[2,3-d]pyridazin-4-amine;

7-(5-fluoro-2-methylphenyl)-N-((3aR,5s,6aS)-2-((tetrahydro-2H-pyran-4-yl)methyl-d2) octahydrocyclopenta[c]pyrrol-5-yl)thieno[2,3-d]pyridazin-4-amine;

7-(4,4-difluoropiperidin-1-yl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-((S)-3-methylpiperidin-1-yl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

4-(4,4-difluoropiperidin-1-yl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine;

4-(2,5-difluorophenyl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine;

4-(2-fluorophenyl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine;

4-(3-fluorophenyl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine;

4-(4-fluorophenyl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine; and 4-(2,5-difluorophenyl)-N-((3aR,5s,6aS)-2-((tetrahydro-2H-pyran-4-yl) methyl-d2)octahydrocyclopenta[c]pyrrol-5-yl)phthalazin-1-amine;

or a pharmaceutically acceptable salt thereof.

Compound names and/or structures can be assigned/determined by using the Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

Compounds have a 3,3a,4,5,6,6a-hexahydro-1H-cyclopenta[c]pyrrole core structure that has a plane of symmetry as in the following two representative structures.

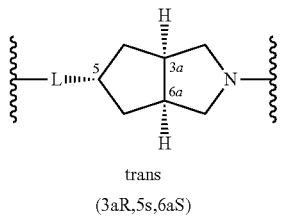

trans
(3aR,5s,6aS)

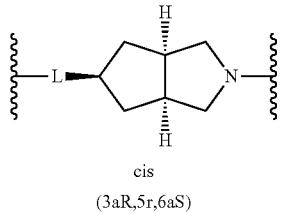

cis
(3aR,5r,6aS)

These structures are considered meso since A and B are superimposable with their respective mirror images. The 3a, 5, and 6a stereochemical designations are used herein for symmetrical structures of type A and B to designate relative stereochemistry between the ring fusion and the 5-position. Thus, when drawn in the orientation depicted above 3aR, 5s,6aS refers to trans relative stereochemistry between the 5-position substituent and the ring fusion, and 3aR,5r,6aS refers to cis relative stereochemistry between the 5-position substituent and the ring fusion. The lower case s and r designations at the 5-position refer to pseudo assymetry as described by G.P. Moss in "Basic terminology of stereochemistry (IUPAC Recommendations)" in Pure and Applied Chemistry (1996), 68 (12) 2193-2222. The person skilled in the art will understand that when structures A and B are drawn as the respective mirror images, chemical naming programs may, depending on the program, reverse the stereochemical designation for 3a and 6 positions from R to S and S to R, respectively, but that the pseudo asymmetry at the 5-position remains invariant, due to R having priority over S according to priority rules and the reversal of the carbons having R and S designations. Compounds of formula (I) may have a 5-position substituent in a trans configuration or a cis configuration, or may be prepared as a mixture of trans and cis.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations: AcOH is acetic acid; BMS is borane dimethyl sulfide complex; Boc is tert-butyloxycarbonyl; BrettPhos-Pd-G$^3$ is [(2-di-cyclohexylphosphino-3,6-dimethoxy-2',4', 6'-triisopropyl-1,1'-biphenyl)-2-(2'-amino-1,1'-biphenyl)]palladium(II) methanesulfonate (CAS Number 1470372-59-8); t-BuXPhos is 2-di-tert-butylphosphino-2',4',6'-triisopropylbiphenyl; DAST is diethylaminosulfur trifluoride; DCE is 1,2-dichloroethane; DCM is dichloromethane; DIBAL is diisobutylaluminum hydride; DIEA and DIPEA both refer to N,N-diisopropylethylamine; DMF is N,N-dimethylformamide; HATU is 2-(7-aza-1H-benzotriazole-1-yl)-1,1,3,3-tetramethyluronium hexafluorophosphate; m-CPBA is meta-chloroperoxybenzoic acid; MeOH is methanol; MSCl is methanesulfonyl chloride; NaBH(OAc)$_3$ and STAB both refer to sodium triacetoxyborohydride; rt or r.t. is room temperature; NMP is N-methyl-2-pyrrolidone; Pd(dppf)Cl$_2$ is [1,1'-Bis(diphenylphosphino)ferrocene]dichloropalladium(II); Pd$_2$(dba)$_3$ is tris(dibenzylideneacetone) dipalladium(0); RuPhos-Pd-G$^3$ is (2-dicyclohexylphosphino-2',6'-diisopropoxy-1,1'-biphenyl)[2-(2'-amino-1,1'-biphenyl)]palladium(II) methanesulfonate (CAS Number 1445085-77-7); t-BuOH is tert-butyl alcohol; t-BuOK is potassium tert-butoxide; TBAI is tetrabutylammonium iodide; THF is tetrahydrofuran; and TosMIC is toluenesulfonylmethyl isocyanide.

Compounds of formula (I) may be synthesized as shown in the following schemes.

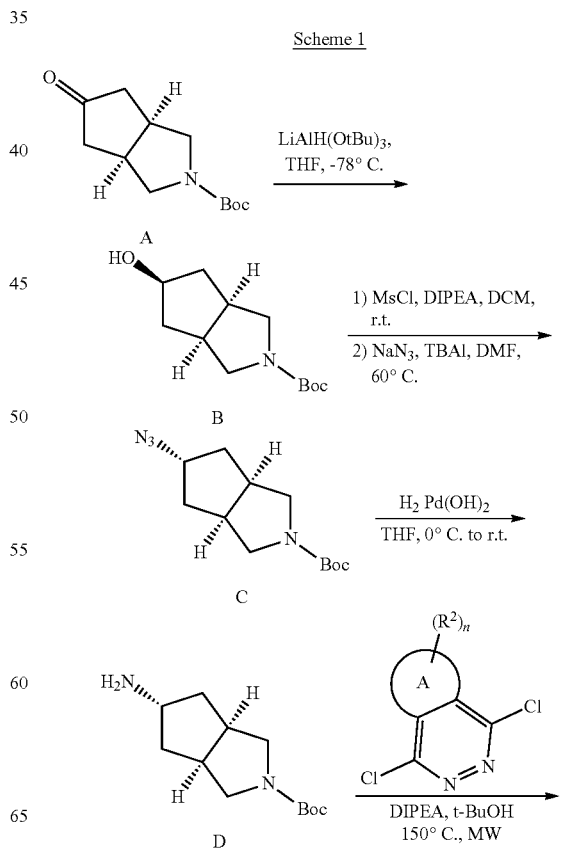

-continued

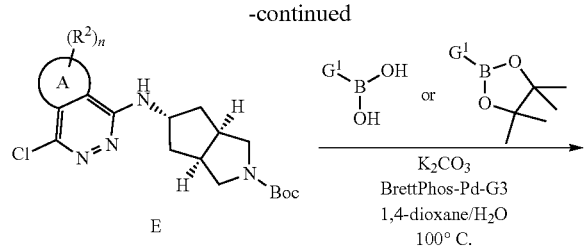

E

Scheme 2

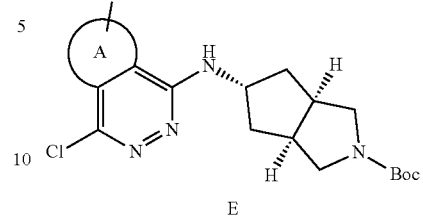

E

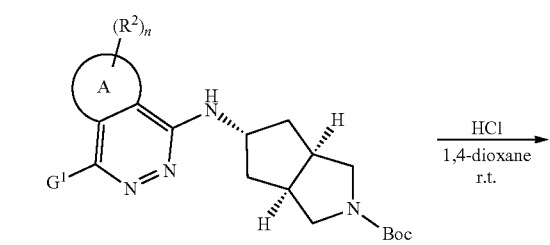

F

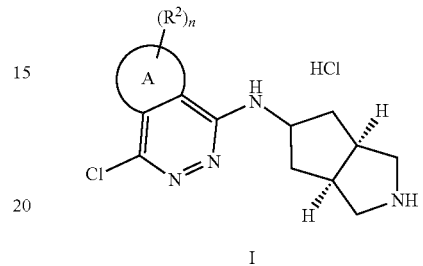

I

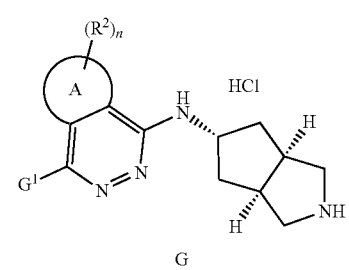

G

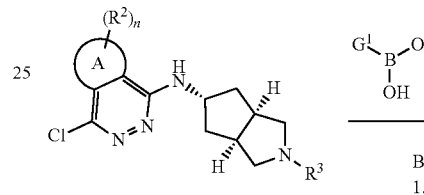

J

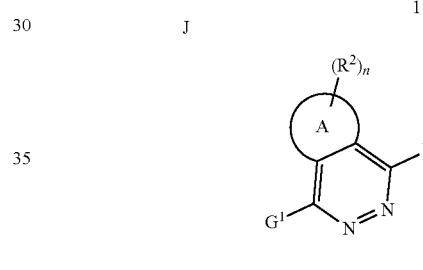

H

Scheme 2 illustrates an alternate synthesis route to compounds of formula H, wherein the reductive amination and boronic acid coupling steps are reversed. Deprotection of compound E under acid conditions provides compound I, which may be reacted with suitable aldehydes or ketones corresponding to $R^3$ by reductive amination to provide compounds J, wherein $R^{3'}$ is $G^{2'}$, —$L^1$—$G^2$, —$C_{2-6}$alkylene—$R^{3a}$, or $C_{3-7}$alkyl. In turn, reaction of compounds J with suitable boronic acids or esters may provide compounds H.

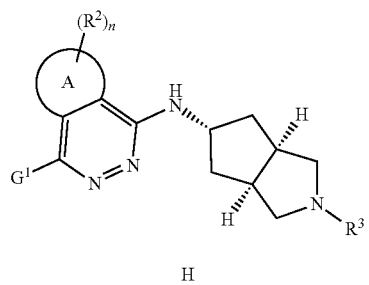

H

As shown in Scheme 1, cis-tert-butyl 5-oxohexahydrocyclopenta[c]pyrrole-2(1H)-carboxylate (compound A; CAS #146231-54-1, Synthonix, Catalog #B8253) can be reduced (e.g., lithium tri-t-butoxy aluminum hydride) to form compound B, which can then be converted to the corresponding azide compound C. Reduction to the amine provides compound D, which can be reacted with a dichloropyridazine compound to generate compound E. Coupling with a suitable boronic acid or ester may provide compound F, which may be deprotected (e.g., with hydrochloric acid) to generate compound G. Compound G may be reacted with suitable aldehydes or ketones corresponding to $R^3$ by reductive amination to provide H, wherein $R^3$ is $G^{2'}$, —$L^1$—$G^2$, —$C_{2-6}$alkylene—$R^{3a}$, or $C_{3-7}$alkyl and $G^{2'}$, is the carbocyclyl or heterocyclyl of $G^2$.

Scheme 3

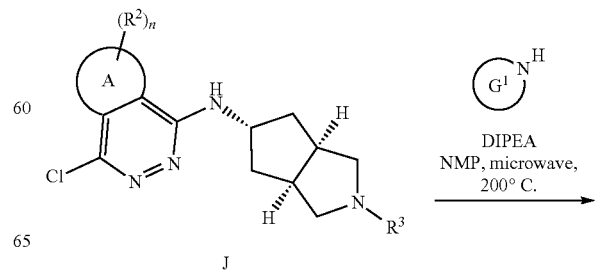

J

-continued

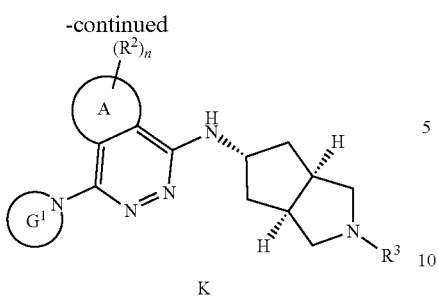

K

As provided in Scheme 3, reaction of compounds J with a cyclic secondary amine corresponding to a heterocyclic $G^1$ (e.g., morpholine, piperidine) provides compounds of formula K.

Scheme 4

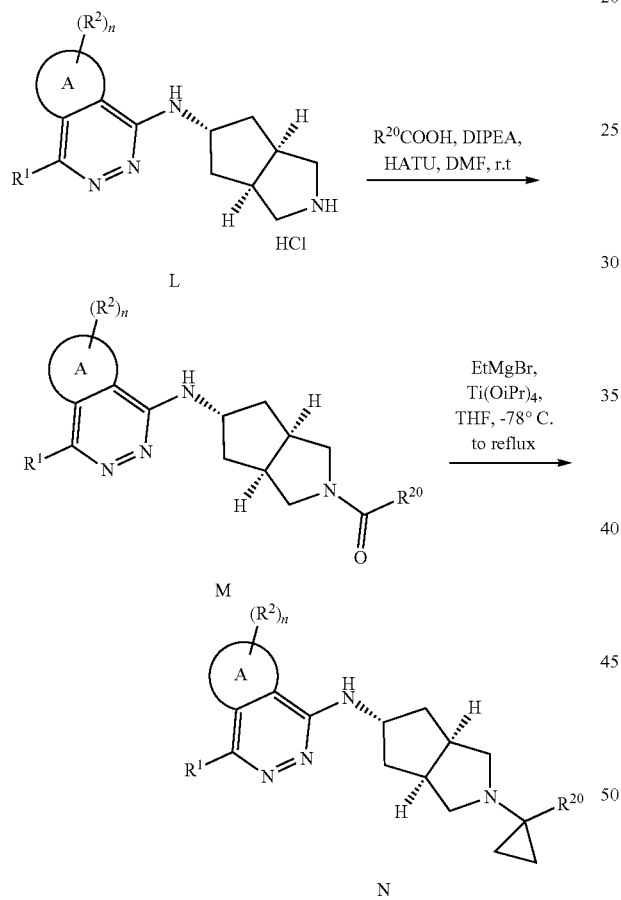

As shown in Scheme 4, reaction of compounds L with a carboxylic acid $R^{20}CO_2H$ under standard amide bond forming conditions may provide amides M. Suitable reaction conditions include reacting L (1 equiv.) with the carboxylic acid (1.2 equiv.) in the presence of DIPEA (3 equiv.) and HATU (1.5 equiv.) in DME at room temperature. Amides M may react with a titanacyclopropane generated in situ from an ethyl Grignard and $Ti(OiPr)_4$ (Kulinkovich-de Meijere reaction) to provide cyclopropyl compounds of formula N. Suitable reaction conditions include reacting a solution of ethylmagnesium bromide (5 equiv., 1.0 M solution) in THF with titanium(IV) isopropoxide (2.1 equiv.) at −78° C. for 30 min under an inert atmosphere, and adding compound M (1 equiv. in THF), followed by warming to r.t. and then stirring at reflux for 1 h. In Scheme 4, $R^{20}$ is $G^2$, $—L^1—G^2$, an alkyl group (e.g., $C_{1-4}$alkyl), $—C_{1-3}$alkylene$—OR^{13}$, or $—C_{1-3}$alkylene$—N(R^{13})_2$, wherein $G^2$, $L^1$, and $R^{13}$ are as defined herein.

Scheme 5

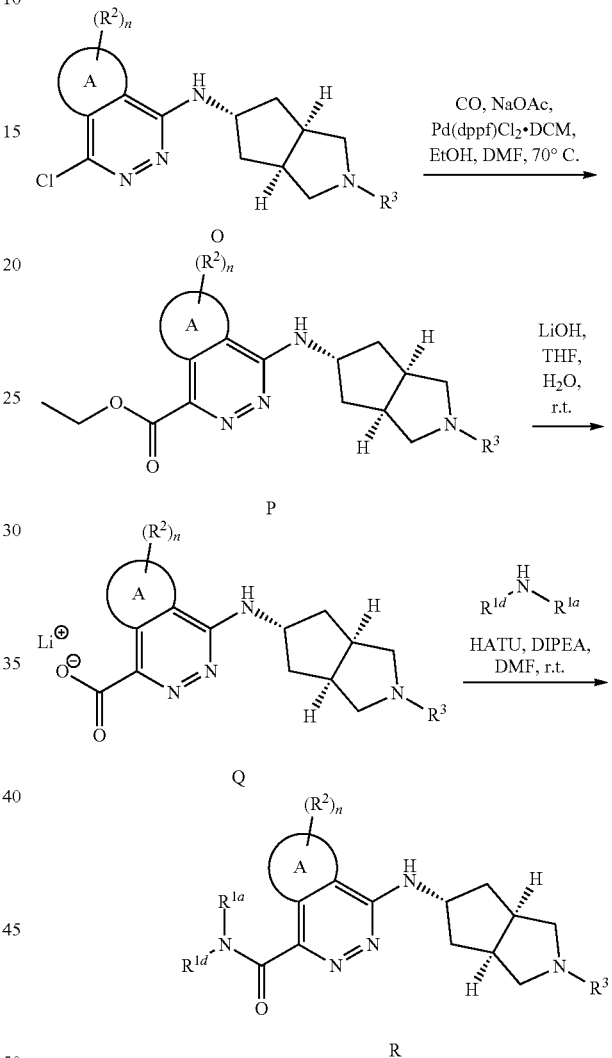

As shown in Scheme 5, carbonylation of compounds O may provide compounds P. Suitable reaction conditions include reacting compound O (1 equiv.), sodium acetate (2 equiv.), and $Pd(dppf)Cl_2·DCM$ (0.1 equiv.) in EtOH:DMF (5:1), followed by degassing and stirring under an atmosphere of CO (balloon) at 70° C. for 3 h. Compound P may by hydrolyzed under basic conditions to Q. Suitable reaction conditions include reacting P with LiOH (3 equiv.) in THF:$H_2O$ (1:1) at r.t. for 1 h. Compound Q (or its acid) may be converted to the corresponding amide R using standard amide bond forming reaction conditions, such as reacting Q (1 equiv.) with an amine (2 equiv.) in DMF with DIPEA (5 equiv.) and HATU (1.5 equiv.) at r.t. In Scheme 5, $R^{1a}$ is hydrogen, $G^1$, $—C_{1-3}$alkylene$—G^1$, $C_{1-6}$alkyl, or $C_{1-6}$haloalkyl, and $R^{1a}$ is as defined herein.

Scheme 6

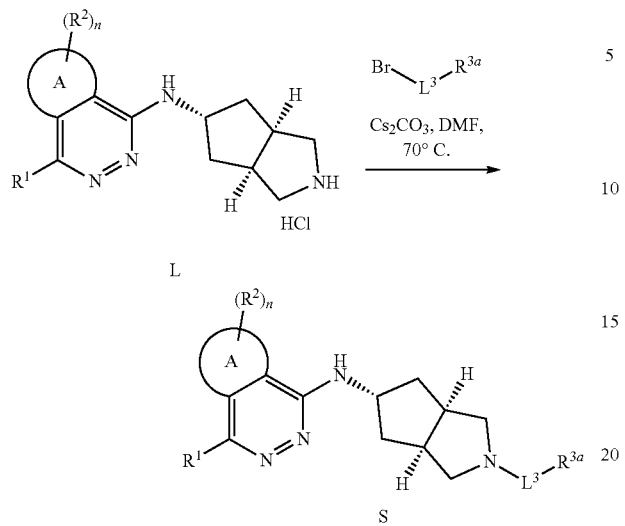

As shown in Scheme 6, compounds of formula L may be alkylated using standard secondary amine alkylation conditions to provide tertiary amines S, wherein $L^3$ is an alkylene group and $R^{3a}$ is as defined herein. Suitable reaction conditions include reacting L (1 equiv.) with a suitable bromide (e.g., 1-bromo-3-methoxypropane, 5 equiv.) in DMF with cesium carbonate (3 equiv.) at 70° C. until completion of the reaction.

Scheme 7

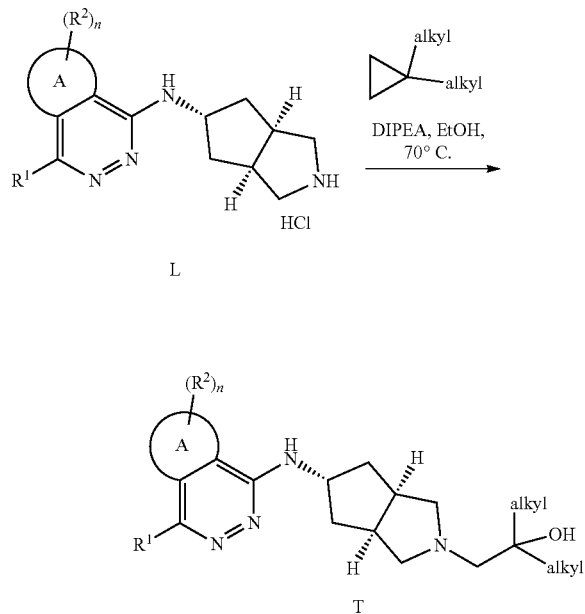

As shown in Scheme 7, secondary amine compounds L may be reacted with epoxides under basic conditions to provide hydroxy compounds T. Suitable reaction conditions include reacting L (1 equiv.) with an epoxide such as isobutylene oxide (3 equiv.) in EtOH in the presence of DIPEA (3 equiv.) at 70° C. until completion of the reaction.

Scheme 8

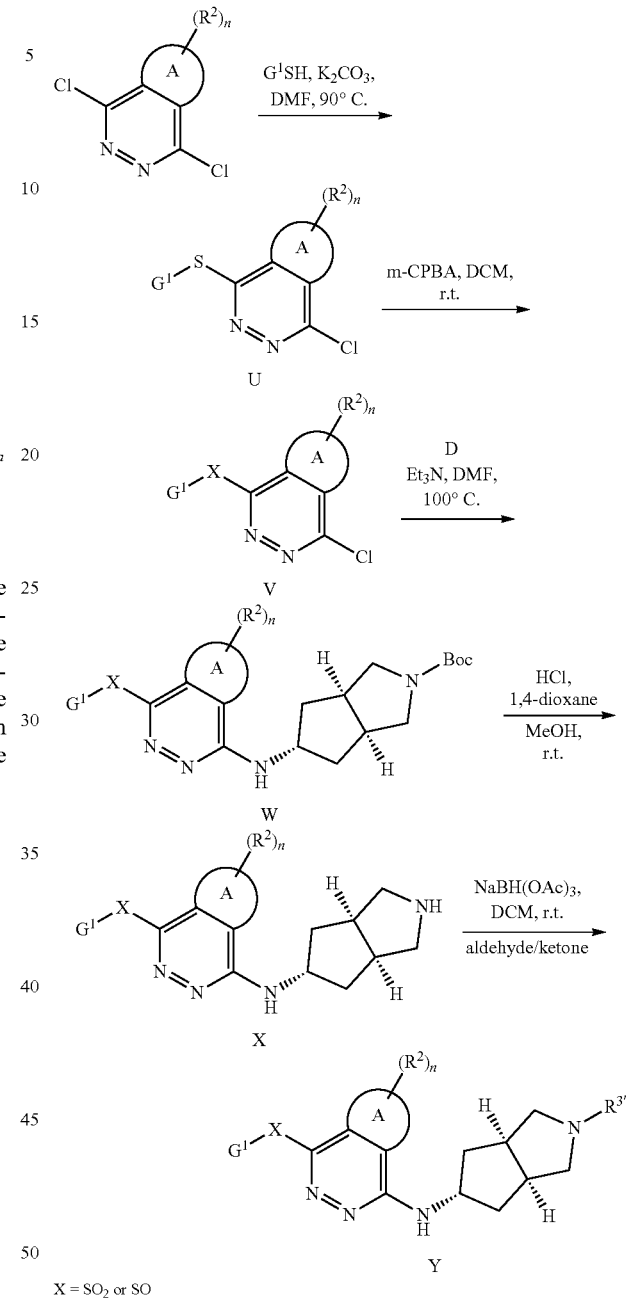

X = SO$_2$ or SO

Compounds of formula Y, wherein X is SO$_2$ or S(O) may be prepared in a multistep sequence as shown in Scheme 8. Reaction of an optionally substituted dichloropyridazine with an appropriate thiol under basic conditions may provide compounds U. Suitable reaction conditions include reacting the dichloropyridazine (1 equiv.) with $G^1$—SH (1 equiv.) in DMF in the presence of a base such as potassium carbonate (3 equiv.) at 90° C. until completion of the reaction. Oxidation of U may provide sulfone or sulfoxide compounds V. Suitable conditions for sulfone formation include reacting U (1 equiv.) with an oxidant such as m-CPBA (2.5 equiv.) in DCM at room temperature until completion of the reaction. Compounds V may be coupled with primary amine D to provide compounds W. Suitable reaction conditions include reaction of D (1.2 equiv.) with V (1 equiv.) in DMF in the presence of a base such as triethyl amine (3 equiv.) at 100° C. until completion of the reaction. Deprotection of W under acidic conditions followed by reductive amination with an aldehyde or ketone may provide compounds Y, wherein $R^{3'}$ is $G^{2'}$ (as defined above), —$L^1$—$G^2$, —$C_{2-6}$alkylene—$R^{3a}$, or $C_{3-7}$alkyl, wherein $L^1$, $G^2$, and $R^{3a}$ are as defined herein.

Scheme 9

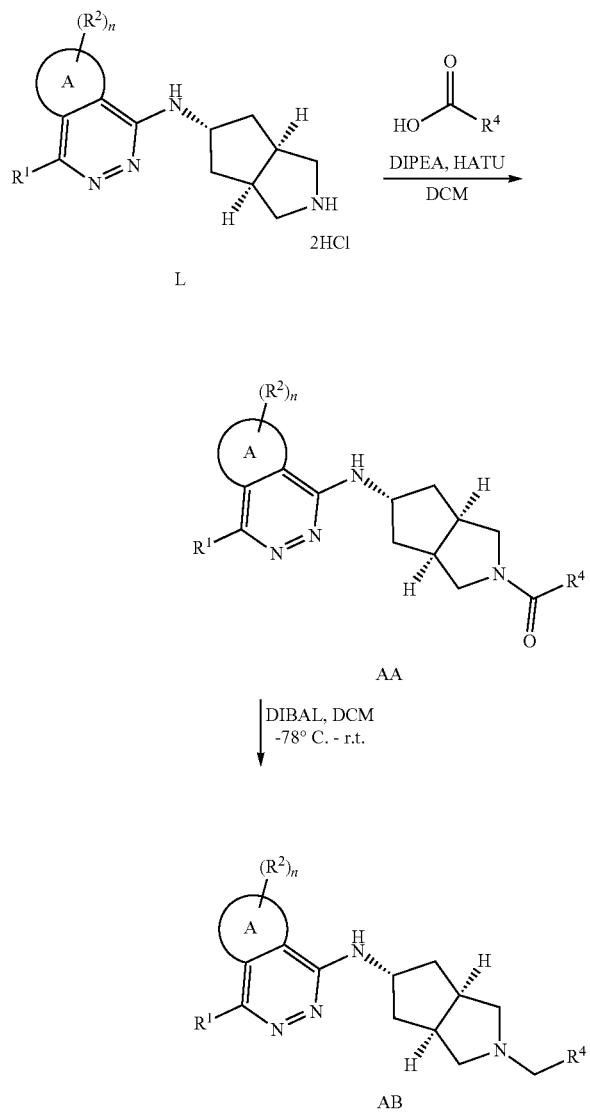

Scheme 10

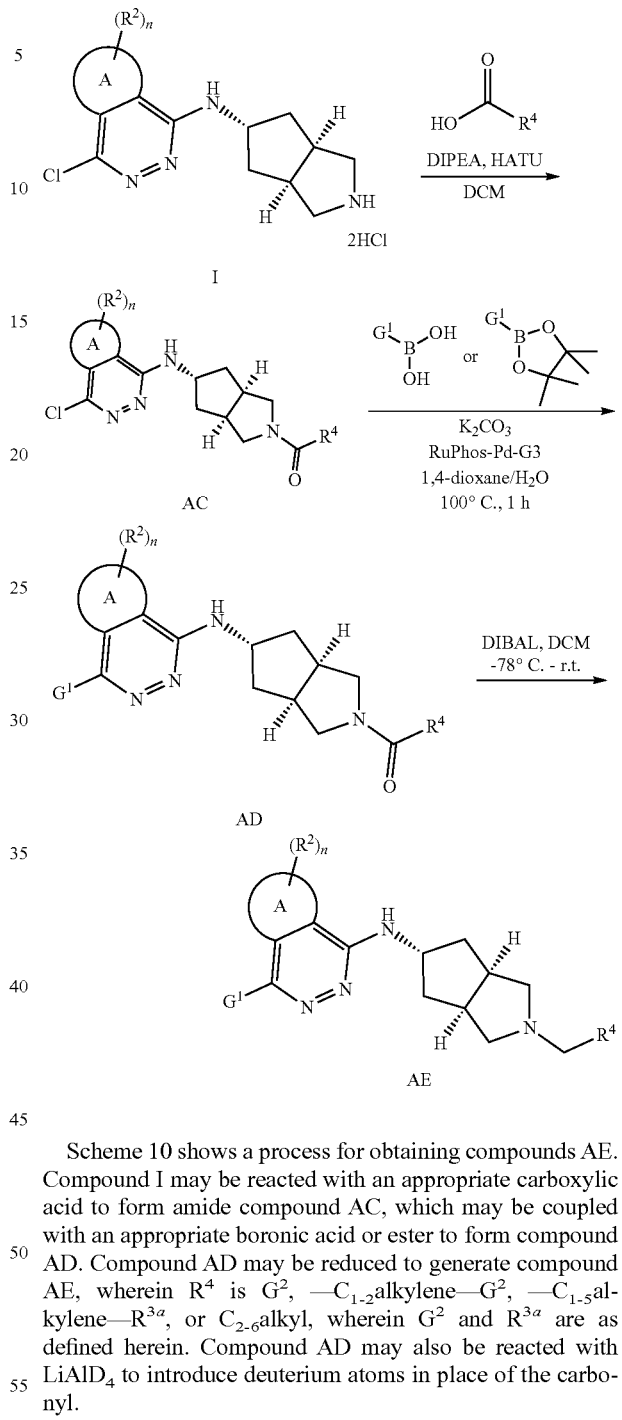

Scheme 10 shows a process for obtaining compounds AE. Compound I may be reacted with an appropriate carboxylic acid to form amide compound AC, which may be coupled with an appropriate boronic acid or ester to form compound AD. Compound AD may be reduced to generate compound AE, wherein $R^4$ is $G^2$, —$C_{1-2}$alkylene—$G^2$, —$C_{1-5}$alkylene—$R^{3a}$, or $C_{2-6}$alkyl, wherein $G^2$ and $R^{3a}$ are as defined herein. Compound AD may also be reacted with LiAlD$_4$ to introduce deuterium atoms in place of the carbonyl.

As shown in Scheme 9, compound L may be reacted with an appropriate carboxylic acid to form amide compound AA, which may be reduced to generate compound AB, wherein $R^4$ is $G^2$, —$C_{1-2}$alkylene—$G^2$, —$C_{1-5}$alkylene—$R^{3a}$, or $C_{2-6}$alkyl, wherein $G^2$ and $R^{3a}$ are as defined herein. Compound AA may also be reacted with LiAlD$_4$ to introduce deuterium atoms in place of the carbonyl. The process of Scheme 9 may be used where $R^1$ is chloro. Compounds AA having $R^1$=chloro may be subjected to a Suzuki reaction prior to carbonyl reduction to prepare, compounds having $R^1$=$G^1$ (e.g. aryl, heteroaryl). Suitable Suzuki reaction conditions include those generally outlined in Schemes 1 and 2 and as described in the Examples herein.

Scheme 11

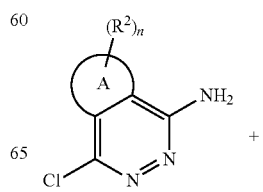

-continued

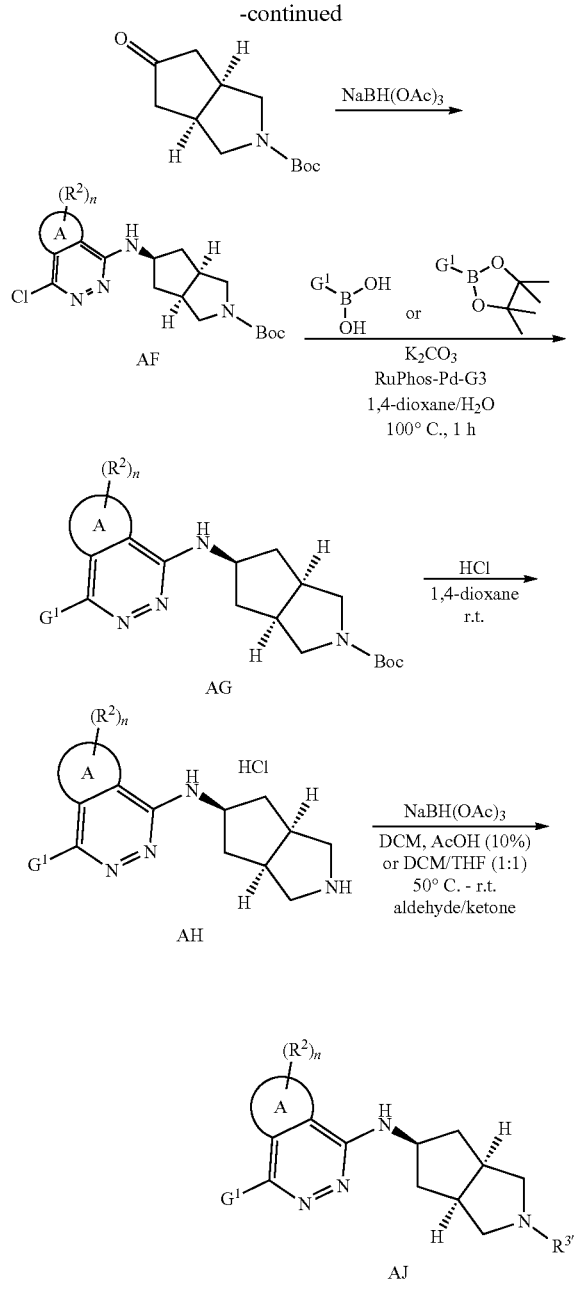

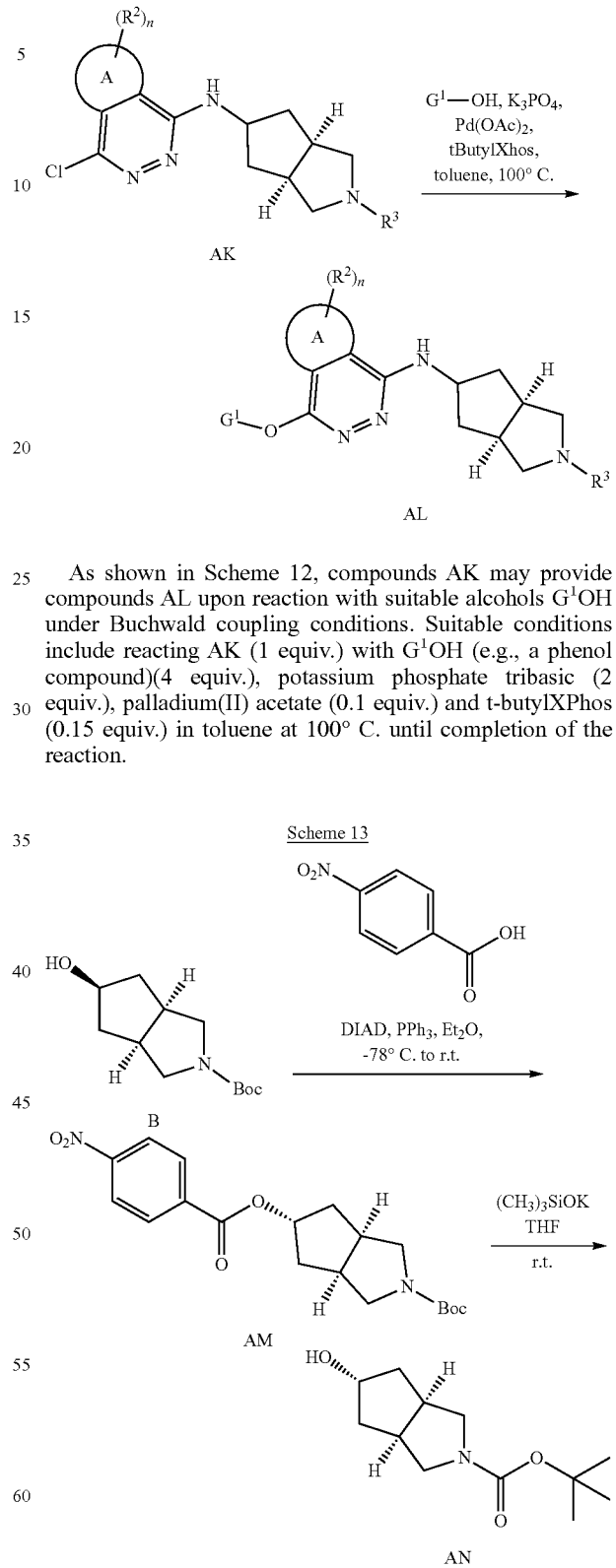

As shown in Scheme 11, an amino-chloropyridazine may be reacted with cis-N-Boc-5-oxo-octahydrocyclopenta[c]pyrrole to generate compound AF. Suitable reaction conditions include reacting the amino-chloropyridazine (5 equiv.) with the ketone (1 equiv.) and sodium triacetoxyborohydride (4 equiv.) in THF:DCE (1:1) at 60° C. until reaction completion. AF may be coupled with an appropriate boronic acid or ester to form compound AG. Deprotection (e.g., with hydrochloric acid) generates compounds AH, and reaction with a suitable aldehyde/ketone generates compound AJ, wherein R$^{3'}$ is G$^{2'}$ (as defined above), —L$^1$—G$^2$, —C$_{2-6}$alkylene—R$^{3a}$, or C$_{3-7}$alkyl, wherein L$^1$, G$^2$, and R$^{3a}$ are as defined herein. The intermediates AH may also be reacted according to procedures shown in Schemes 4, 6, and 7 to provide additional compounds of the invention and/or useful intermediates.

As shown in Scheme 12, compounds AK may provide compounds AL upon reaction with suitable alcohols G$^1$OH under Buchwald coupling conditions. Suitable conditions include reacting AK (1 equiv.) with G$^1$OH (e.g., a phenol compound)(4 equiv.), potassium phosphate tribasic (2 equiv.), palladium(II) acetate (0.1 equiv.) and t-butylXPhos (0.15 equiv.) in toluene at 100° C. until completion of the reaction.

As shown in Scheme 13, compound B may be converted to compound AM, using a Mitsunobu reaction, and cleaved to AN. Compounds B and AN may be elaborated to compounds of the invention by reaction with dichloropyridazine compounds described herein, under basic conditions (e.g., NaH, THF, r.t.), followed by further synthetic processing according to the Schemes and Examples herein.

Scheme 14

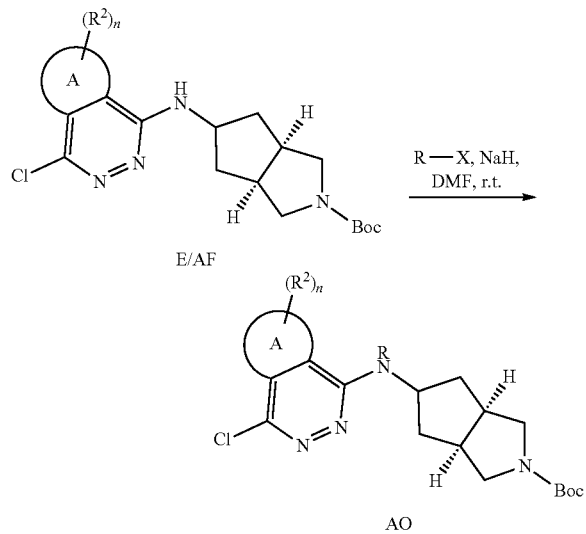

E/AF

AO

Scheme 14 illustrates a route to intermediates AO by N-alkylation of intermediates E/AF under basic conditions in the presence of a suitable alkylating agent (e.g., X is Cl, Br, I, OMs, OTs, OTf). Compounds AO may be useful to prepare further compounds of the invention according to the synthetic methods of the Schemes and Example herein.

The reaction of compounds G, I, L, X, and AH with ketones by reductive amination may be facilitated by addition of an acid like acetic acid to the solvent mixture (e.g., DMC-THF) and heating to 40° C. for about an hour. A representative solvent ratio of DCM:THF:AcOH is (3:3: 0.5).

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity $M_4$ is the most highly expressed mAChR subtype in the striatum and its expression is similar in rodents and primates. Due to a lack of selective $M_4$ antagonists, mechanistic understanding of the role of $M_4$ has been guided by biochemical and genetic studies, as well as the use of highly selective $M_4$ positive allosteric modulators (PAMs). Highly selective $M_4$ PAMs induce robust decreases in behavioral responses to psychomotor stimulants that act by increasing striatal DA levels. Furthermore, genetic deletion of $M_4$ increases exploratory locomotor activity, potentiates locomotor responses to amphetamine and other stimulants, and eliminates effects of $M_4$PAMs on locomotor activity and these effects are also observed with selective deletion of $M_4$ from striatal spiny projection neurons that express the D1 subtype of DA receptor (D1-SPNs). In vivo microdialysis studies reveal that administration of $M_4$ PAMs reduces amphetamine-induced DA release in the dorsal and ventral striatum and fIVIRI studies show that $M_4$ PAMs reverse amphetamine-induced increases in cerebral blood flow (CBV) in striatum and other basal ganglia nuclei. More recently, fast-scanning cyclic voltammetry (FSCV) and genetic studies, demonstrated that $M_4$ PAMs act, at least in part, by inhibition of DA release from presynaptic DA terminals in the striatum through release of an endocannabinoid from striatal spiny projection neurons (SPNs) and activation of CB2 cannabinoid receptors on DA terminals.

$M_4$ is heavily expressed in a subset of SPNs that also express the $D_1$ subtype of DA receptor ($D_1$DR), which form the direct pathway (D1-SPNs) sending inhibitory projections to the substantia nigra pars reticulata (SNr). Interestingly, $D_1$DRs activate a unique GTP-binding protein in D1-SPNs, termed $G_{\alpha olf}$ that couples $D_1$Rs to activation of adenylyl cyclase, formation of cAMP, and activation of protein kinase A (PKA). This signaling pathway is critical for many of the behavioral actions of DA-mediated activation of motor activity Interestingly, $M_4$ couples to $G\alpha_{i/o}$ proteins, which inhibit adenylyl cyclase and have the potential to directly counteract inhibit $D_1$ receptor signaling and effects on motor function. These studies raise the possibility that, in addition to inhibition of DA release, $M_4$ PAMs may directly inhibit D1R-mediated signaling in $D_1$-SPNs by direct inhibition of cAMP formation and this could also contribute to the powerful inhibitory effect of selective $M_4$ activation of DA signaling in the basal ganglia. Consistent with this, $M_4$ PAMs inhibit locomotor-stimulating effects of a direct acting $D_1$ agonist. Furthermore, a series of pharmacological, genetic, and molecular/cellular studies reveal that this response is mediated by inhibition of $D_1$DR signaling in D1-SPNs. Thus, the primary action of $M_4$ PAMs on $D_1$DR signaling is not in the striatum, but on GABAergic terminals of $D_1$-SPNs in the SNr, where activation of $D_1$DRs induces a robust increase in GABA release. This challenges the widespread view that cholinergic regulation of striatal function is almost exclusively mediated through ACh released from tonically active, striatal cholinergic interneurons (ChIs) and raises the possibility that cholinergic innervation of the SNr from cholinergic projections from the pedunculopontine nucleus may also play a critical role in regulating motor activity and other functions of the basal ganglia direct pathway. Together, these data suggest that in addition to inhibiting DA release, $M_4$ activation also acts postsynaptically in $D_1$-expressing SPNs to inhibit motor function.

Consistent with a prominent role of $M_4$ as the primary mAChR subtype involved in regulating motor function, multiple reports indicate that the locomotor-activating effects of the mAChR antagonist scopolamine are dramatically reduced in $M_4$ knockout mice, but not the other four mAChR subtypes ($M_{1-3,5}$). Furthermore, haloperidol-induced catalepsy, a model of parkinsonian motor disability, is reduced in $M_4$ knockout mice as compared to wild-type controls. Evaluation of the anti-parkinsonian effects of scopolamine, by assessing effects of this compound on catalepsy induced by the DA receptor antagonist haloperidol, display robust catalepsy that was completely reversed by scopolamine in WT mice. The reversal by scopolamine was uncommonly robust and more pronounced than we observe with agents targeting a number of other targets being evaluated for potential antiparkinsonian effects, including metabotropic glutamate (mGlu) receptors $mGlu_4$ or $mGlu_5$, $A_2A$ adenosine receptors, and NMDA receptors. Importantly, scopolamine was ineffective in reducing catalepsy in $M_4$ KO mice, suggesting that the anti-cataleptic effect of scopolamine requires actions on mAChR $M_4$. Taken together with the extensive studies of $M_4$ modulation of basal ganglia and motor function, these studies provide compelling evidence that $M_4$ is the dominant mAChR subtype involved in the antiparkinsonian effects of non-selective mAChR antagonists and provide support for discovery and development of selective $M_4$ antagonists for treatment of neurodegenerative disease such as PD, dystonia, tardive dyskinesia and other movement disorders.

Despite advances in mAChR research, there is still a scarcity of compounds that are potent, efficacious and selective antagonists of the $M_4$ mAChR. Highly selective $M_4$ antagonists represent a new therapeutic approach for the treatment of neurodegenerative diseases including PD, dystonia, tardive dyskinesia and other movement disorders and may offer the clinical benefit of scopolamine, without the adverse effects mediated by pan-mAChR inhibition.

In some embodiments, the disclosed compounds are antagonists of mAChR $M_4$. Such activity can be demonstrated by methodology known in the art. For example, antagonism of mAChR $M_4$ activity can be determined by measurement of calcium flux in response to agonist, e.g. acetylcholine, in cells loaded with a $Ca^{2+}$-sensitive fluorescent dye (e.g., Fluo-4) and co-expression of a chimeric or promiscuous G protein. In some embodiments, the calcium flux can be measured as an increase in fluorescent static ratio. In some embodiments, antagonist activity can be analyzed as a concentration-dependent increase in the $EC_{80}$ acetylcholine response (i.e. the response of mAChR $M_4$ at a concentration of acetylcholine that yields 80% of the maximal response).

In some embodiments, the disclosed compounds antagonize mAChR $M_4$ as a decrease in calcium fluorescence in mAChR $M_4$-transfected CHO-K1 cells in the presence of the compound, compared to the response of equivalent CHO-K1 cells in the absence of the compound. In some embodiments, a disclosed compound antagonizes the mAChR $M_4$ response with an $IC_{50}$ of less than about 10 µM, less than about 5 µM, less than about 1 82 M, less than about 500 nM, of less than about 100 nM, or less than about 50 nM. In some embodiments, the mAChR $M_4$-transfected CHO-K1 cells are transfected with human mAChR $M_4$. In some embodiments, the mAChR $M_4$-transfected CHO-K1 cells are transfected with rat mAChR $M_4$. In some embodiments, the mAChR $M_4$-transfected CHO-K1 cells are transfected with mAChR $M_4$ from dog or cynomolgus monkey.

The disclosed compounds may antagonize mAChR $M_4$ response in mAChR $M_4$-transfected CHO-K1 cells with an $IC_{50}$ less than the $IC_{50}$ for one or more of mAChR $M_1$, $M_2$, $M_3$ or $M_5$-transfected CHO-K1 cells. That is, a disclosed compound can have selectivity for the mAChR $M_4$ receptor vis-à-vis one or more of the mAChR $M_1$, $M_2$, $M_3$ or $M_5$ receptors. For example, in some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_1$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, a disclosed compound can antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, a disclosed compound can antagonize mAChR $M_4$ response with an $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, or greater than about 500-fold less than that for the mAChR $M_1$, $M_2$, $M_3$, or $M_5$ receptors.

The disclosed compounds may antagonize mAChR $M_4$ response in $M_4$-transfected CHO-K1 cells with an $IC_{50}$ less than about 10 μM and exhibit a selectivity for the $M_4$ receptor vis-à-vis one or more of the mAChR $M_1$, $M_2$, $M_3$, or $M_5$ receptors. For example, in some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, 10-fold less, 20-fold less, 30-fold less, 50-fold less, 100-fold less, 200-fold less, 300-fold less, 400-fold less, or greater than about 500-fold less than that for mAChR $M_1$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_2$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_3$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with an $IC_{50}$ of about 5-fold less, about 10-fold less, about 20-fold less, about 30-fold less, about 50-fold less, about 100-fold less, about 200-fold less, about 300-fold less, about 400-fold less, or greater than about 500-fold less than that for mAChR $M_5$. In some embodiments, the compound can have an $IC_{50}$ of less than about 10 μM, of less than about 5 μM, of less than about 1 μM, of less than about 500 nM, of less than about 100 nM, or of less than about 50 nM; and the compound can also antagonize mAChR $M_4$ response with $IC_{50}$ of 5-fold less, about 10-fold less, about 20-fold less, about 30-fold less than that for the $M_2$-$M_5$ receptors, of about 50-fold less, about 100-fold less, about 200-fold less, about 300-fold less, about 400-fold less, $M_2$, $M_3$, or $M_5$ receptors, or greater than about 500-fold less than that for the mAChR $M_1$, $M_2$, $M_3$, or $M_5$ receptors.

In vivo efficacy for disclosed compounds in models that predict antiparkinsonian activity can be measured in a number of preclinical rat models. For example, disclosed compounds may reverse deficits in motor function induced by the dopamine receptor antagonist in mice or rats. Also, these compounds may reverse deficits in motor function that are observed with other manipulations that reduce dopaminergic signaling, such as selective lesions of dopamine neurons. In addition, it is possible that these compounds will have efficacy in animal models of dystonia and may increase attention, cognitive function, and measures of motivation in animal models.

3. Pharmaceutical Compositions and Formulations

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp.587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The pharmaceutical composition or formulation may antagonize mAChR $M_4$ with an $IC_{50}$ of less than about 10 µM, less than about 5 M, less than about 1 µM, less than about 500 nM, or less than about 100 nM. The pharmaceutical composition or formulation may antagonize mAChR $M_4$ with an $IC_{50}$ of between about 10 µM and about 1 nM, about 1 µM and about 1 nM, about 100 nM and about 1 nM, or between about 10 nM and about 1 nM.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I).

4. Methods of Use

The disclosed compounds, pharmaceutical compositions and formulations may be used in methods for treatment of disorders, such as neurological and/or psychiatric disorders, associated with muscarinic acetylcholine receptor dysfunction. The disclosed compounds and pharmaceutical compositions may also be used in methods for decreasing muscarinic acetylcholine receptor activity in a mammal. The methods further include cotherapeutic methods for improving treatment outcomes. In the methods of use described herein, additional therapeutic agent(s) may be administered simultaneously or sequentially with the disclosed compounds and compositions.

a. Treating Disorders

The disclosed compounds, pharmaceutical compositions and formulations may be used in methods for treating, preventing, ameliorating, controlling, reducing, or reducing the risk of a variety of disorders, or symptoms of the disorders, in which a patient would benefit from antagonism of mAChR $M_4$. In some embodiments, the disorder may be a neurodegenerative disorder, a movement disorder, or a brain disorder. The methods may comprise administering to a subject in need of such treatment a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof.

Disorders in which a patient would benefit from antagonism of mAChR $M_4$ may include neurodegenerative disorders and movement disorders. For example, exemplary disorders may include Parkinson's disease, drug-induced Parkinsonism, dystonia, Tourette's syndrome, dyskinesias (e.g., tardive dyskinesia or levodopa-induced dyskinesia), schizophrenia, cognitive deficits associated with schizophrenia, excessive daytime sleepiness (e.g., narcolepsy), attention deficit hyperactivity disorder (ADHD), Huntington's disease, chorea (e.g., chorea associated with Huntington's disease), cerebral palsy, and progressive supranuclear palsy.

In some embodiments, the disclosure provides a method for treating motor symptoms in a subject having Parkinson's disease, comprising administering to a subject in need thereof a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the motor symptoms are selected from bradykinesia, tremor, rigidity, gait dysfunction, and postural instability. The method may treat the motor symptoms, control the motor symptoms, and/or reduce the motor symptoms in the subject.

In some embodiments, the disclosure provides a method for treating motor symptoms in a subject having dystonia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. The method may treat the motor symptoms, control the motor symptoms, and/or reduce the motor symptoms in the subject. For example, treatment may reduce muscle contractions or spasms in a subject having dystonia.

In some embodiments, the disclosure provides a method for treating motor symptoms in a subject having tardive dyskinesia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. The method may treat the motor symptoms, control the motor symptoms, and/or reduce the motor symptoms in the subject. For example, treatment may reduce involuntary movements in a subject having tardive dyskinesia.

In some embodiments, the disclosure provides a method of preventing or delaying tardive dyskinesia in a subject at risk of developing tardive dyskinesia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the subject may be a subject being treated with a neuroleptic medication (e.g., a typical antipsychotic or an atypical antipsychotic), a dopamine antagonist, or an antiemetic.

In some embodiments, the disclosure provides a method of treating catalepsy in a subject suffering from schizophrenia, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the subject suffering from schizophrenia may have catalepsy induced by a neuroleptic agent (e.g., a typical antipsychotic or an atypical antipsychotic).

In some embodiments, the disclosure provides a method of treating a brain disorder characterized by altered dopamine and cholinergic signaling that could benefit from antagonism of mAChR $M_4$, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. For example, the treatment may increase motivation or goal-directed behavior in patients suffering from disorders characterized by reduced motivation for goal-directed behavior, such as schizophrenia and other brain disorders.

In some embodiments, the disclosure provides a method for increasing wakefulness and/or reducing excessive daytime sleepiness in a subject in need thereof, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the subject is a subject suffering from narcolepsy.

In some embodiments, the disclosure provides a method of increasing attention in a subject (e.g., a subject suffering from an attention deficit disorder such as ADHD) in a subject in need thereof, comprising administering to the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof.

In some embodiments, the disclosure provides a method for treating motor symptoms in a subject having a drug-induced movement disorder, comprising administering the subject a therapeutically effective amount of the compound of formula (I) or a pharmaceutically acceptable salt thereof, or a pharmaceutical composition comprising a therapeutically effective amount of a compound of formula (I) or a pharmaceutically acceptable salt thereof. In some embodiments, the drug-induced movement disorder is selected from drug-induced parkinsonism, tardive dyskinesia, tardive dystonia, akathisia, myoclonus, and tremor. The method may treat the motor symptoms, control the motor symptoms, and/or reduce the motor symptoms in the subject.

The compounds and compositions may be further useful in a method for the prevention, treatment, control, amelioration, or reduction of risk of the diseases, disorders and conditions noted herein. The compounds and compositions may be further useful in a method for the prevention, treatment, control, amelioration, or reduction of risk of the aforementioned diseases, disorders and conditions, in combination with other agents.

In the treatment of conditions such as those that would benefit from antagonism of mAChR $M_4$, an appropriate dosage level may be about 0.01 to 500 mg per kg patient body weight per day, which can be administered in single or multiple doses. The dosage level may be about 0.1 to about 250 mg/kg per day, or about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the disclosure relates to a method for antagonizing the mAChR $M_4$ receptor in at least one cell, comprising the step of contacting the at least one cell with at least one disclosed compound or at least one product of a disclosed method in an amount effective to antagonize mAChR $M_4$ in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for antagonizing the mAChR $M_4$ receptor in a subject, comprising the step of administering to the subject at least one disclosed compound or at least one product of a disclosed method in a dosage and amount effective to antagonize the mAChR $M_4$ receptor in the subject. In some embodiments, the subject is mammalian, for example, human. In some embodiments, the mammal has been diagnosed with a need for mAChR $M_4$ antagonism prior to the administering step. In some embodiments, the mammal has been diagnosed with a need for mAChR $M_4$ antagonism prior to the administering step. In some embodiments, the method further comprises the step of identifying a subject in need of mAChR $M_4$ antagonism.

b. Antagonism of the Muscarinic Acetylcholine Receptor

In some embodiments, the disclosure relates to a method for antagonizing mAChR $M_4$ in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In some embodiments, antagonism of the muscarinic acetylcholine receptor decreases muscarinic acetylcholine receptor activity.

In some embodiments, the compound administered antagonizes mAChR $M_4$ with an $IC_{50}$ of less than about 10 less than about 5 less than about 1 less than about 500 nM, or less than about 100 nM. In some embodiments, the compound administered antagonizes mAChR $M_4$ with an $IC_{50}$ of between about 10 μM and about 1 nM, about 1 μM and about 1 nM, about 100 nM and about 1 nM, or about 10 nM and about 1 nM.

In some embodiments, the mammal is a human. In some embodiments, the mammal has been diagnosed with a need for reduction of muscarinic acetylcholine receptor activity prior to the administering step. In some embodiments, the method further comprises the step of identifying a mammal in need of reducing muscarinic acetylcholine receptor activity. In some embodiments, the antagonism of the muscarinic acetylcholine receptor treats a disorder associated with muscarinic acetylcholine receptor activity in the mammal. In some embodiments, the muscarinic acetylcholine receptor is mAChR $M_4$.

In some embodiments, antagonism of the muscarinic acetylcholine receptor in a mammal is associated with the treatment of a disorder associated with a muscarinic receptor dysfunction, such as a disorder disclosed herein. In some embodiments, the muscarinic receptor is mAChR $M_4$.

In some embodiments, the disclosure provides a method for antagonizing the muscarinic acetylcholine receptor in a cell, comprising the step of contacting the cell with an effective amount of at least one disclosed compound or a pharmaceutically acceptable salt thereof. In some embodiments, the cell is mammalian (e.g., human). In some embodiments, the cell has been isolated from a mammal prior to the contacting step. In some embodiments, contacting is via administration to a mammal.

c. Cotherapeutic Methods

The present disclosure is further directed to administration of a mAChR $M_4$ antagonist, such as a selective mAChR $M_4$ antagonist, for improving treatment outcomes. That is, in some embodiments, the disclosure relates to a cotherapeutic method comprising a step of administering to a mammal an effective amount and dosage of at least one disclosed compound, or a pharmaceutically acceptable salt thereof.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In some embodiments, administration may improve treatment outcomes in the context of physical or occupational therapy. Administration in connection with physical or occupational therapy can be continuous or intermittent. Administration need not be simultaneous with therapy and can be before, during, and/or after therapy. For example, physical or occupational therapy can be provided within 1, 2, 3, 4, 5, 6, 7 days before or after administration of the compound. As a further example, physical or occupational therapy can be provided within 1, 2, 3, or 4 weeks before or after administration of the compound. As a still further example, physical or occupational therapy can be provided before or after administration within a period of time of 1, 2, 3, 4, 5, 6, 7, 8, 9, or 10 half-lives of the administered compound.

It is understood that the disclosed cotherapeutic methods can be used in connection with the disclosed compounds, compositions, kits, and uses.

d. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In some embodiments, the compound can be employed in combination with any other agent that is used to treat a disorder described herein, such as a standard of care therapy for a disorder that would benefit from mAChR $M_4$ antagonism, such as a disorder described herein. For example, in some embodiments, the compound can be employed in combination with a Parkinsonian drug (e.g., L-DOPA, or carbidopa/levodopa) an mGlu$_4$ positive allosteric modulator, an mGlu$_5$ negative allosteric modulator, an $A_2A$ inhibitor, a T-type calcium channel antagonist, a VMAT2 inhibitor, a muscle relaxant (e.g., baclofen), an anticholinergic agent, an antiemetic, a typical or atypical neuroleptic agent (e.g., risperidone, ziprasidone, haloperidol, pimozide, fluphenazine), an antihypertensive agent (e.g., clonidine or guanfacine), a tricyclic antidepressant (e.g., amitriptyline, butriptyline, clomipramine, desipramine, dosulepin, doxepin, imipramine, iprindole, lofepramine, nortriptyline, protriptyline, or trimipramine) an agent that increases extracellular dopamine levels (e.g., amphetamine, methylphenidate, or lisdexamfetamine), an agent for treating excessive daytime sleepiness (e.g., sodium oxybate or a wakefulness-promoting agent such as armodafinil or modafinil), and a norepinephrine reuptake inhibitor (including selective NRIs, e.g., atomoxetine, and non-selective NRIs, e.g., bupropion).

e. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GelucireTM). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. Kits

In one aspect, the disclosure provides a kit comprising at least one disclosed compound or a pharmaceutically acceptable salt thereof, or a pharmaceutical composition comprising at least one disclosed compound or a pharmaceutically acceptable salt thereof and one or more of:

(a) at least one agent known to increase mAChR $M_4$ activity;

(b) at least one agent known to decrease mAChR $M_4$ activity;

(c) at least one agent known to treat a disorder associated with mAChR $M_4$, such as a disorder described herein; and (d) instructions for administering the compound.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may further comprise information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Examples

All NMR spectra were recorded on a 400 MHz AMX Bruker NMR spectrometer. $^1H$ chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 µm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Abbreviations used in the examples that follow are:
AcOH is acetic acid;
Boc is tert-butyloxycarbonyl;
BrettPhos-Pd-G$^3$ is [(2-di-cyclohexylphosphino-3,6-dimethoxy-2',4',6'-triisopropyl-1, 1,1'-biphenyl)-2-(2'-amino-1,1'-biphenyl)]palladium(II) methanesulfonate (CAS Number 1470372-59-8);
DCE is 1,2-dichloroethane;
DCM is dichloromethane;
DIPEA is N,N-diisopropylethylamine;
DMF is N,N-dimethylformamide;
DMSO is dimethylsulfoxide;
eq or equiv is equivalent(s);
EtOAc is ethyl acetate;
EtOH is ethanol;
Et$_3$N is triethylamine;
HATU is 2-(7-aza-1H-benzotriazole-1-yl)-1,1,3,3-tetramethyluronium hexafluorophosphate;
h or h. is hour(s);
hex is hexane;
IPA is isopropyl alcohol;
m-CPBA is meta-chloroperoxybenzoic acid;
LCMS is liquid chromatography mass spectrometry;
MeCN is acetonitrile;
MeOH is methanol;
min or min. is minute(s);
NMP is N-methyl-2-pyrrolidone;
Pd(dppf)Cl$_2$ is [1,1'-Bis(diphenylphosphino)ferrocene]dichloropalladium(II);
RP-HPLC is reverse phase high-performance liquid chromatography;
RuPhos-Pd-G$^3$ is (2-dicyclohexylphosphino-2',6'-diisopropoxy-1,1'-biphenyl) [2-(2'-amino-1,1'-biphenyl)]palladium(II) methanesulfonate (CAS Number 1445085-77-7);
rt, RT, or r.t. is room temperature;
SFC is supercritical fluid chromatography;
TFA is trifluoroacetic acid;
THF is tetrahydrofuran.

Example 1. tert-Butyl (3aR,5s,6aS)-5-amino-3,3a,4,5,6,6a-hexahydro-1H-cyclopenta[c]pyrrole-2-carboxylate.

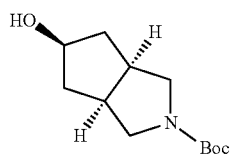 [SMILES: CC(C)(C)OC(=O)N1C[C@H]2C[C@@H](O)C[C@H]2C1]

tert-Butyl (3aR,5r,6aS)-5-hydroxy-3,3a,4,5,6,6a-hexahydro-1H-cyclopenta[c]pyrrole-2-carboxylate. To a solution of tert-butyl (3aR,6aS)-5-oxohexahydrocyclopenta[c]pyrrole-2(1H)-carboxylate (10.0 g, 44.4 mmol) in THF (300 mL) at −78° C. was added a solution of 1.0 M lithium tri-tert-butoxyaluminum hydride solution (53.3 mL, 53.3 mmol) dropwise. The resulting solution was stirred at −78° C. for 2 h, after which time the reaction mixture was warmed to 0° C. and quenched with the slow addition of H$_2$O (17.0 mL), 1 M NaOH solution (17.0 mL) and H$_2$O (51.0 mL) sequentially. The mixture was stirred at 0° C. for 1 h, after which time solids were removed by filtration with diethyl ether (3×200 mL). The filtrate was diluted with EtOAc (500 mL) and sat. NH$_4$Cl solution (300 mL), and the aqueous layer was extracted with EtOAc (3×500 mL). The combined organic extracts were dried with MgSO$_4$, filtered and concentrated under reduced pressure to give a crude mixture of the title compound as a yellow oil which was carried to the next step without further purification. $^1$H-NMR (400 MHz, CDCl) δ4.30 (pent, J=6.4 Hz, 1H), 3.54-3.46 (m, 2H), 3.34 (dd, J=11.2, 3.7 Hz, 2H), 2.65-2.56 (m, 2H), 2.20-2.13 (m, 2H), 1.53-1.47 (m, 2H), 1.45 (s, 9H); d.r. =97:3; ESI-MS=[M+H]$^+$−tButyl=172.0.

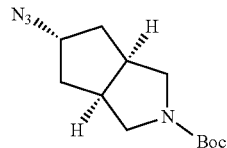

tert-Butyl (3aR,5s,6aS)-5-azido-3,3a,4,5,6,6a-hexahydro-1H-cyclopenta[c]pyrrole-2-carboxylate. To a solution of tert-butyl (3aR,5r,6aS)-5-hydroxyhexahydrocyclopenta[c]pyrrole-2(1H)-carboxylate (10.1 g, 44.4 mmol) in DCM (250 mL), mesyl chloride (4.12 mL, 53.3 mmol), 4-dimethylaminopyridine (0.06 mL, 0.44 mmol), and N,N-diisopropylethylamine (11.6 mL, 66.6 mmol) were added. The reaction mixture was stirred at r.t. overnight. Upon completion, the reaction mixture was quenched with sat. NaHCO$_3$ (100 mL), and extracted with DCM (3×200 mL). The combined organic extracts were dried with Na$_2$SO$_4$, filtered, and concentrated under reduced pressure to give a crude mixture of the mesylate intermediate as an oil which was carried to the next step without further purification. ES-MS=[M+H]$^{+-tButyl}$=250.0.

A mixture of tert-butyl (3aR,5r,6aS)-5-((methylsulfonyl)oxy)hexahydrocyclopenta[c]pyrrole-2(1H)-carboxylate (13.6 g, 44.4 mmol), sodium azide (7.2 g, 111.0 mmol), and tetrabutylammonium iodide (16.4 mg, 0.04 mmol) in DMF (200 mL) was stirred at 60° C. After stirring overnight, the reaction was cooled to r.t. and diluted with EtOAc (200 mL) and H$_2$O (100 mL). The organic layer was washed with H$_2$O, and the aqueous layer was back extracted 1× with EtOAc (200 mL). The combined organic extracts were dried with Na$_2$SO$_4$, and the solvents were filtered and concentrated under reduced pressure. The crude residue was purified by column chromatography on silica gel (0-100% EtOAc in hexanes) to provide the title compound as a clear oil (6.9 g, 62% over 3 steps). $^1$H-NMR (400 MHz, CDCl) δ4.14-4.10 (m, 1H), 3.50-3.48 (m, 2H), 3.22-3.16 (m, 2H), 2.84-2.78 (m, 2H), 2.03-1.97 (m, 2H), 1.76-1.68 (m, 2H), 1.45 (s, 9H); ES-MS=[M+H]$^{+-tButyl}$=197.0.

49

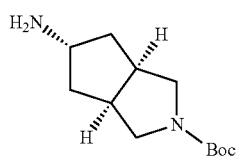

tert-Butyl (3aR,5s,6aS)-5-amino-3,3a,4,5,6,6a-hexahydro-1H-cyclopenta[c]pyrrole-2-carboxylate. tert-Butyl (3aR,5s,6a5)-5-azido-3,3a,4,5,6,6a-hexahydro-1H-cyclopenta[c]pyrrole-2-carboxylate (6.4 g, 25.3 mmol) was dissolved in THF (400 mL), and 20% wt Pd(OH)$_2$/C (1.8 g, 2.5 mmol) was added. The resulting mixture was stirred under H$_2$ (balloon) at 0° C. for 8 h, then slowly warmed to r.t. and stirred overnight, after which time the reaction mixture was filtered through a pad of Celite with EtOAc, and concentrated under reduced pressure. The crude residue was purified by column chromatography on silica gel (0-100% DCM, MeOH, NH$_4$OH (89:10:1) in DCM) to provide the title compound as a solid (5.3 g, 93%). $^1$H-NMR (400 MHz, MeOD) δ3.54-3.43 (m, 3H), 3.33-3.32 (m, 2H), 3.17-3.12 (m, 2H), 2.86-2.80 (m, 2H), 1.81-1.75 (m, 2H), 1.70-1.62 (m, 2H), 1.47 (s, 9H); ES-MS [M+H]$^+$=227.0.

Example 2. tert-Butyl (3aR,5s,6aS)-5-hydroxyhexahydrocyclopenta[c]pyrrole-2(1H)-carboxylate.

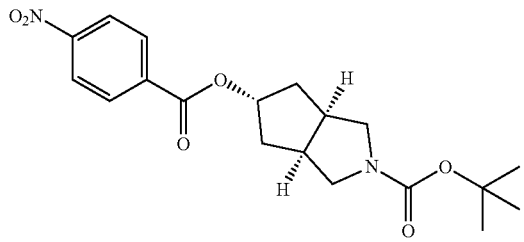 [SMILES: CC(C)(C)OC(=O)N1C[C@H]2C[C@H](OC(=O)c3ccc([N+](=O)[O-])cc3)C[C@H]2C1]

tert-Butyl (3aR,5s,6aS)-5-((4-nitrobenzoyl)oxy) hexahydrocyclopenta[c]pyrrole-2(1H)-carboxylate. To a solution of tert-butyl (3aR,5r,6aS)-5-hydroxyhexahydrocyclopenta[c]pyrrole-2(1H)-carboxylate (1.01 g, 4.44 mmol), triphenylphosphine (1.40 g, 5.33 mmol), and 4-nitrobenzoic acid (890 mg, 5.33 mmol) in diethyl ether (15 mL) was added diisopropyl azodicarboxylate (1.05 mL, 5.33 mmol) at −78° C. The reaction mixture was warmed to r.t. and stirred for 18 h, after which time the reaction mixture was quenched with the addition of MeOH (2 mL), and stirred for 15 min. Solvents were concentrated under reduced pressure, and the crude residue was purified by column chromatography (3-30% EtOAc in hexanes) to give the title compound as a colorless oil that solidified upon standing (1.67 g, 100%, 80% purity after chromatography). ES-MS [M+H −tbutyl]$^+$= 321.3.

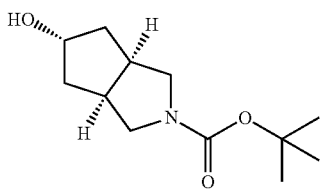 [SMILES: CC(C)(C)OC(=O)N1C[C@H]2C[C@H](O)C[C@H]2C1]

tert-Butyl (3aR,5s,6aS)-5-hydroxyhexahydrocyclopenta[c]pyrrole-2(1H)-carboxylate. tert-Butyl (3aR,5s,6aS)-5-((4-nitrobenzoyl)oxy)hexahydrocyclopenta[c]pyrrole-2(1H)-carboxylate (1.67 g, 4.44 mmol) was dissolved in THF (30 mL) and potassium trimethylsilanolate (2.85 g, 22.2 mmol) was added. The resulting cloudy brown mixture was stirred at r.t. for 2 h, after which time solvents were concentrated under reduced pressure, and the crude residue was diluted in DCM and H$_2$O. The aqueous layer was extracted with DCM, and the combined organic extracts were dried with MgSO$_4$. Solvents were filtered and concentrated under reduced pressure, and the crude residue was purified by column chromatography (0-1% MeOH in DCM) to give the title compound as a white solid (435 mg, 43%). $^1$H-NMR (400 MHz, CDCl) δ4.50-4.45 (m, 1H), 3.54-3.46 (m, 2H), 3.16 (br, 2H), 2.89-2.79 (m, 2H), 1.92-1.86 (m, 2H), 1.73-1.66 (m, 2H), 1.45 (s, 9H). ES-MS [M+H −tbutyl]$^+$=172.4.

Example 3. 4-(2-Fluorophenyl)-N-((3aR,5s,6aS)-2-((tetrahydro-2H-pyran-4-yl) methyl)octahydrocyclopenta[c]pyrrol-5-yl)thieno[2,3-d]pyridazin-7-amine.

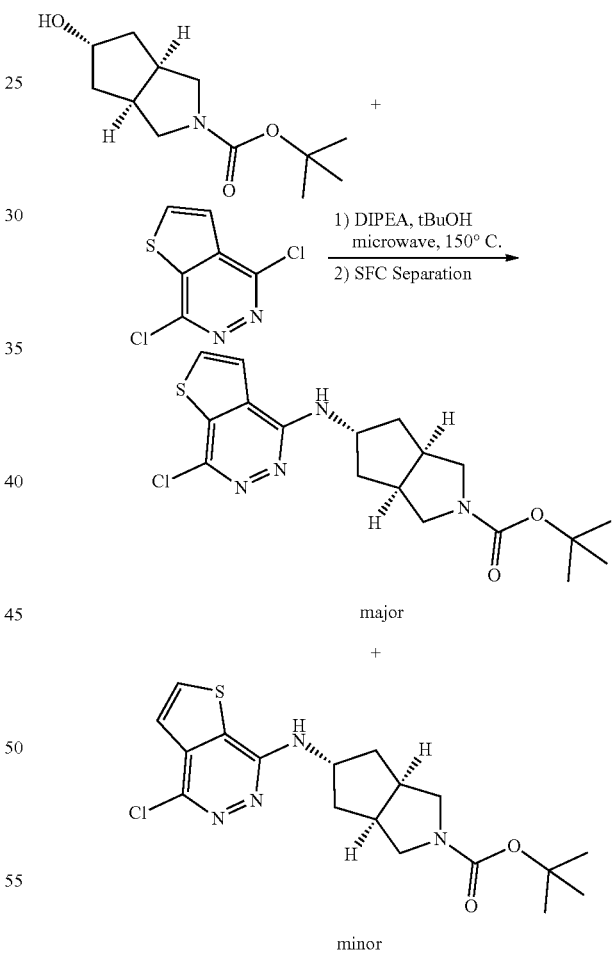

tert-Butyl (3aR,5s,6aS)-5-((7-chlorothieno[2,3-d]pyridazin-4-yl) amino)hexahydrocyclopenta[c]pyrrole-2 (1H)-carboxylate and tert-butyl (3aR,5s,6aS)-5-((4-chlorothieno[2,3-d]pyridazin-7-yl)amino)hexahydrocyclopenta[c]pyrrole-2(1H)-carboxylate. To a solution of tert-butyl (3aR, 5s,6aS)-5-aminohexahydrocyclopenta[c]pyrrole-2(1H)-carboxylate (250 mg, 1.10 mmol, 1 eq) and 4,7-dichlorothieno[2,3-d]pyridazine (453 mg, 2.21 mmol, 2 eq)

in t-butanol (2 mL) was added DIPEA (0.58 mL, 3.31 mmol, 3 eq). The resulting solution was heated under microwave irradiation at 150° C. for 2 h, after which time solvents were concentrated, and crude residue was purified by column chromatography (3-80% EtOAc in hexanes) to give a mixture of chlorothienopyridazine regioisomers, which were further separated by supercritical fluid chromatography (4.6×250 mm Lux Cellulose-4 column; 25% isocratic gradient with ethanol co-solvent, 80 mL/min at 40° C.) to give both title compounds as colorless oils. Major product: (183 mg, 42%). ¹H-NMR (400 MHz, CDCl) δ7.74 (d, J=5.4 Hz, 1H), 7.34 (d, J=5.4 Hz, 1H), 4.86-4.77 (m, 2H), 3.65-3.55 (m, 2H), 3.27-3.15 (m, 2H), 2.89-2.80 (m, 2H), 2.24-2.09 (m, 2H), 1.94-1.81 (m, 2H), 1.46 (s, 9H). ES-MS [M+H]⁺= 395.4. Minor product: (92 mg, 21%). ¹H-NMR (400 MHz, CDCl) δ7.72 (d, J=5.3 Hz, 1H), 7.50 (d, J=5.3 Hz, 1H), 4.87-4.78 (m, 1H), 4.53 (d, J=6.5 Hz, 1H), 3.65-3.55 (m, 2H), 3.28-3.16 (m, 2H), 2.90-2.81 (m, 2H), 2.23-2.09 (m, 2H), 1.95-1.83 (m, 2H), 1.47 (s, 9H). ES-MS [M+H]⁺= 395.4.

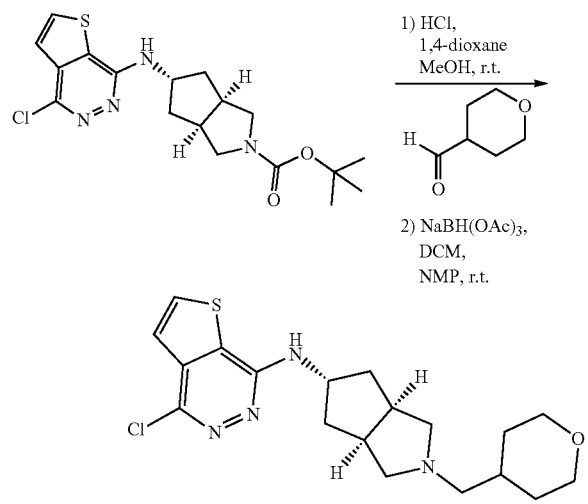

4-Chloro-N-((3aR,5s,6aS)-2-((tetrahydro-2H-pyran-4-yl)methyl)octahydrocyclopenta[c]pyrrol-5-yl)thieno[2,3-d]pyridazin-7-amine. To a solution of tert-butyl (3aR,5s,6aS)-5-((4-chlorothieno[2,3-d]pyridazin-7-yl) amino)hexahydrocyclopenta[c]pyrrole-2(1H)-carboxylate (92 mg, 0.23 mmol) in 1,4-dioxane (1 mL) and methanol (0.25 mL) was added dropwise 4 M HCl in dioxanes solution (1.5 mL). After 2 h at r.t., solvents were concentrated under reduced pressure, and the resulting white solid was dried under vacuum and used without further purification (77 mg, 100%). ES-MS [M+H]⁺=295.2. To a solution of the hydrochloride salt (77 mg, 0.23 mmol, 1 eq) in DCM (1 mL) and NMP (0.5 mL) was added 4-oxanaldehyde (80 mg, 0.70 mmol, 3 eq), followed by sodium triacetoxyborohydride (148 mg, 0.70 mmol, 3 eq). After 2 h at r.t., the reaction mixture was quenched with sat. NaHCO₃, and extracted with 3:1 chloroform/IPA (v/v). The combined organic extracts were filtered through a phase separator and concentrated. The crude residue was purified by RP-HPLC (25-65% MeCN in 0.05% NH₄OH aqueous solution over 10 min). Fractions containing product were concentrated to give the title compound as a white solid (69 mg, 75%). ¹H-NMR (400 MHz, CDCl) δ7.71 (d, J=5.3 Hz, 1H), 7.50 (d, J=5.3 Hz, 1H), 4.85-4.76 (m, 1H), 4.46 (d, J=7.2 Hz, 1H), 3.97 (dd, J=11.2, 3.9 Hz, 2H), 3.89 (td, J=11.9, 1.6 Hz, 2H), 2.78-2.71 (m, 2H), 2.69-2.62 (m, 2H), 2.30 (dd, J=9.0, 3.8 Hz, 2H), 2.26 (d, J=6.7 Hz, 2H), 2.12-2.05 (m, 2H), 1.77-1.65 (m, 5H), 1.35-1.23 (m, 2H). ES-MS [M+H]⁺=393.2.

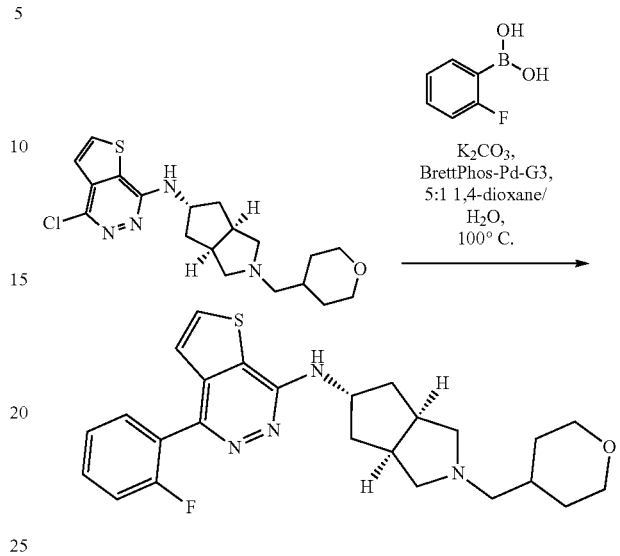

4-(2-Fluorophenyl)-N-((3aR,5s,6aS)-2-((tetrahydro-2H-pyran-4-yl) methyl)octahydrocyclopenta[c]pyrrol-5-yl) thieno[2,3-d]pyridazin-7-amine. 4-Chloro-N-((3aR, 5s,6aS)-2-((tetrahydro-2H-pyran-4-yl)methyl)octahydrocyclopenta[c]pyrrol-5-yl) thieno[2,3-d]pyridazin-7-amine (17 mg, 0.044 mmol, 1 eq), potassium carbonate (18 mg, 0.13 mmol, 3 eq), 2-fluorophenylboronic acid (9.2 mg, 0.066 mmol, 1.5 eq) and BrettPhos-Pd-G³ (4.0 mg, 0.004 mmol, 0.1 eq) were combined in a sealed vial and placed under an inert atmosphere. 5:1 1,4-dioxane/H₂O solution (1 mL, degassed) was then added. The resulting mixture was heated to 100° C. for 1 h, after which time the reaction mixture was cooled to r.t. and diluted with DCM and water. The aqueous layer was extracted with DCM. The combined organic extracts were filtered through a phase separator and concentrated, and crude residue was purified by RP-HPLC (5-35% MeCN in 0.1% TFA aqueous solution over 5 min). Fractions containing product were basified with sat. NaHCO₃, and extracted with DCM. The combined organic extracts were filtered through a phase separator and concentrated to give the title compound as a white solid (6.1 mg, 31%). ¹H-NMR (400 MHz, CDCl) δ7.76 (td, J=7.5, 1.8 Hz, 1H), 7.63 (d, J=5.3 Hz, 1H), 7.45 (m, 1H), 7.33-7.28 (m, 2H), 7.23-7.18 (m, 1H), 4.98-4.89 (m, 1H), 4.53 (d, J=7.2 Hz, 1H), 3.96 (dd, J=11.2, 3.7 Hz, 2H), 3.39 (td, J=11.8, 1.5 Hz, 2H), 2.80-2.74 (m, 2H), 2.73-2.68 (m, 2H), 2.30-2.25 (m, 4H), 2.14 (dd, J=11.7, 5.9 Hz, 2H), 1.80-1.64 (m, 5H), 1.35-1.24 (m, 2H). ES-MS [M+H]⁺=453.4.

Example 4. N-((3aR,5s,6aS)-2-(Tetrahydro-2H-pyran-4-yl) methyl)octahydrocyclopenta[c]pyrrol-5-yl)-7-(2,3,5-trifluorophenyl)thieno[2,3-d]pyridazin-4-amine.

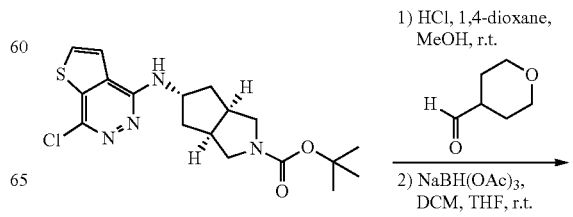

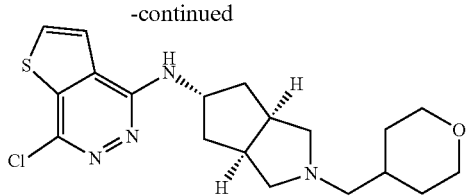

7-Chloro-N-((3aR,5s,6aS)-2-((tetrahydro-2H-pyran-4-yl) methyl)octahydrocyclopenta[c]pyrrol-5-yl)thieno[2,3-d] pyridazin-4-amine. tert-Butyl (3aR,5s,6aS)-5-((7-chlorothieno[2,3-d]pyridazin-4-yl)amino)hexahydrocyclopenta[c] pyrrole-2(1H)-carboxylate (182.8 mg, 0.46 mmol, 1 eq) was dissolved in 1,4-dioxane (2 mL) and methanol (0.5 mL), followed by the dropwise addition of 4M HCl in dioxanes solution (3 mL). After 2 h at r.t., solvents were concentrated under reduced pressure, resulting in a white solid that was further dried under vacuum and used without further purification (153.3 mg, 100%). ES-MS [M+H]$^+$=295.2. The hydrochloride salt (80 mg, 0.24 mmol, 1 eq) and 4-oxanaldehyde (83.3 mg, 0.73 mmol, 3.0 eq) were combined in a vial, and DCM (1.5 ml) and THF (1.5 ml) were added via syringe. After 5 min, sodium triacetoxyborohydride (155.3 mg, 0.73 mmol, 3.0 eq) was added. After 2.5 h at r.t., the reaction was neutralized with sat. NaHCO$_3$ solution, and stirred for 5 min. The aqueous layer was extracted in DCM, dried over MgSO$_4$ and separated through a phase separator. The organic extracts were concentrated and purified by RP-HPLC (5-55% MeCN in 0.05% NH$_4$OH aqueous solution over 10 min). Fractions containing product were concentrated to yield the title compound as a white solid (53 mg, 56%). $^1$H-NMR (400 MHz, CDCl$_3$) δ7.73 (d, J=5.3 Hz, 1H), 7.33 (d, J=5.4 Hz, 1H), 4.86-4.76 (m, 1H), 4.69 (d, J=7.1 Hz, 1H), 3.97 (dd, J=11.9, 3.8 Hz, 2H), 3.39 (td, J=11.8, 1.6 Hz, 2H), 2.83-2.71 (m, 4H), 2.31-2.24 (m, 4H), 2.10 (dd, J=12.7, 5.9 Hz, 2H), 1.76-1.66 (m, 5H), 1.35-1.23 (m, 2H). ES-MS [M+H]$^+$=393.2.

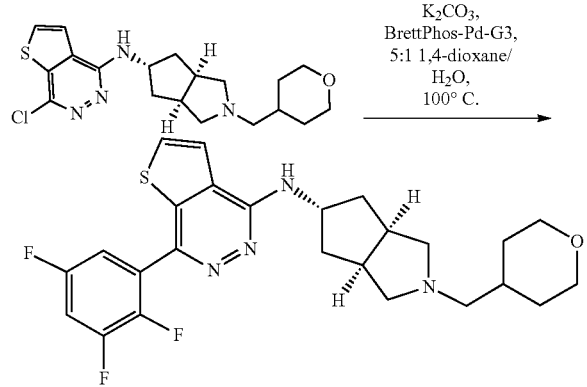

N-((3aR,5s,6aS)-2-(Tetrahydro-2H-pyran-4-yl) methyl) octahydrocyclopenta[c]pyrrol-5-yl)-7-(2,3,5-trifluorophenyl)thieno[2,3-d]pyridazin-4-amine. 7-Chloro-N-((3aR,5s, 6aS)-2-((tetrahydro-2H-pyran-4-yl) methyl) octahydrocyclopenta[c]pyrrol-5-yl)thieno[2,3-d]pyridazin-4-amine (13 mg, 0.03 mmol, 1 eq), 2,3,5-trifluorophenylboronic acid (8.8 mg, 0.05 mmol, 1.5 eq), potassium carbonate (14 mg, 0.1 mmol, 3 eq), and BrettPhos-Pd-G$^3$ (3 mg, 0.003 mmol, 0.1 eq) were combined and sealed in a vial and placed under an inert atmosphere. 5:1 1,4-dioxane/H$_2$O solution (0.7 ml, degassed) was added via syringe and reaction was heated under an inert atmosphere at 100° C. for 1 h. The reaction was then cooled, diluted in H$_2$O and extracted in DCM, and concentrated. The crude residue was purified by RP-HPLC (17-47% MeCN in 0.1% TFA aqueous solution over 4 min). Fractions containing product were basified with sat. NaHCO$_3$ solution, extracted in DCM, and concentrated to yield the title compound as a colorless oil (1.6 mg, 10%). $^1$H-NMR (400 MHz, CDCl3) δ7.73 (d, J=5.4 Hz, 1H), 7.34 (d, J=5.5 Hz, 1H), 7.31-7.26 (m, 1H), 7.08-7.03 (m, 1H), 4.98-4.87 (m, 1H), 4.81 (d, J=7.1 Hz, 1H), 3.96 (dd, J=15.4, 4.3 Hz, 2H), 3.39 (td, J = 10.5, 1.8 Hz, 2H), 2.84-2.71(m, 4H), 2.27 (d, J=5.6 Hz, 4H), 2.15 (dd, J=12.4, 6.3 Hz, 2H), 1.78-1.66 (m, 5H), 1.34-1.25 (m, 2H). ES-MS [M+H]$^+$=485.2.

Example 5. 7-(2,5-Difluorophenyl)-N-((3aR,5s,6aS)-2-((tetrahydro-2H-pyran-4-yl)methyl-d2) octahydrocyclopenta[c]pyrrol-5-yl)thieno[2,3-d]pyridazin-4-amine.

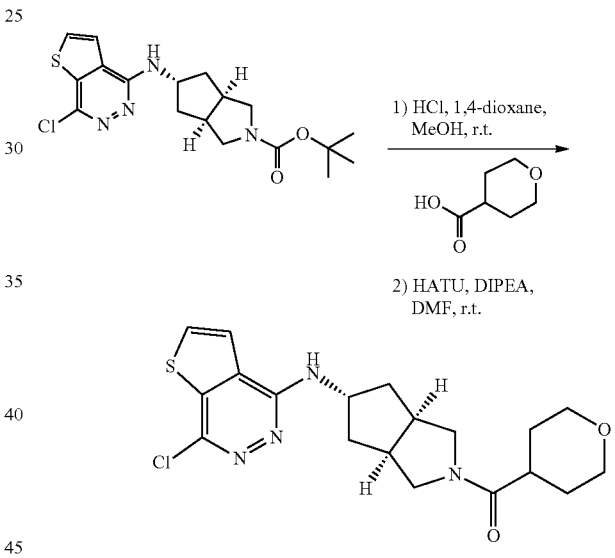

((3aR,5s,6aS)-5-((7-Chlorothieno[2,3-d]pyridazin-4-yl) amino)hexahydrocyclopenta[c]pyrrol-2(1H)-yl)(tetrahydro-2H-pyran-4-yl)methanone. tert-Butyl (3aR,5s,6aS)-5-((7-chlorothieno[2,3-d]pyridazin-4-yl) amino)hexahydrocyclopenta[c]pyrrole-2(1H)-carboxylate (182.8 mg, 0.46 mmol, 1 eq) was dissolved in 1,4-dioxane (2 mL) and methanol (0.5 mL), followed by the dropwise addition of 4M HCl in dioxanes solution (3 mL). After 2 h at r.t., solvents were concentrated under reduced pressure, resulting in a white solid that was further dried under vacuum, and used without further purification (153 mg, 100%). ES-MS [M+H]+= 295.2. The resulting hydrochloride salt (75.4 mg, 0.23 mmol, 1 eq), 4-oxanic acid (59.3 mg, 0.46 mmol, 2.0 eq), and DIPEA (0.16 mL, 0.91 mmol, 4 eq) were combined in a vial followed by the addition of DMF (1.1 mL). After 10 min at r.t., HATU (113 mg, 0.30 mmol, 1.3 eq) was added. The reaction was stirred overnight at r.t., after which time it was purified directly by RP-HPLC (15-65% MeCN in 0.05% NH$_4$OH aqueous solution over 10 min). Fractions containing product were concentrated to yield the title compound as a white solid (48 mg, 52%). $^1$H-NMR (400

MHz, CDCl₃) δ7.75 (d, J=5.4 Hz, 1H), 7.37 (d, J=5.5 Hz, 1H), 4.98-4.91 (m, 1H), 4.84-4.74 (m, 1H), 4.06-3.99 (m, 2H), 3.78 (d, J=9.1 Hz, 1H), 3.74 (dd, J=11.8, 3.3 Hz, 1H), 3.49-3.37 (m, 3H), 3.36 (d, J=5.1 Hz, 1H), 3.02-2.92 (m, 1H), 2.92-2.82 (m, 1H), 2.65-2.43 (m, 1H), 2.29-2.22 (m, 1H), 2.15-2.07 (m, 1H), 1.98-1.84 (m, 4H), 1.70-1.56 (m, 2H). ES-MS [M+H]⁺=407.2.

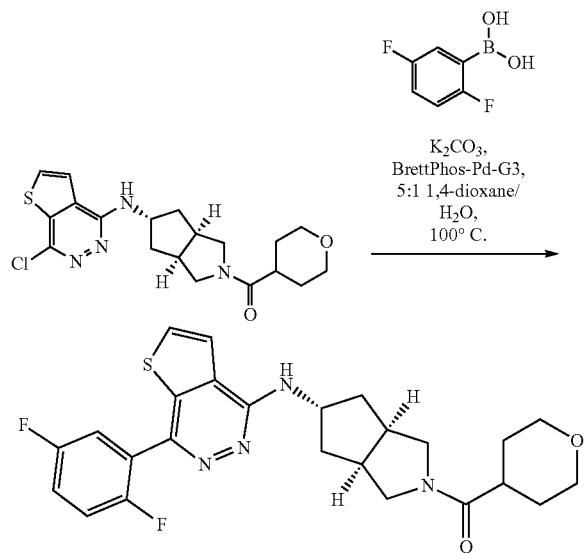

((3aR,5s,6aS)-5-((7-(2,5-Difluorophenyl)thieno[2,3-d]pyridazin-4-yl) amino)hexahydrocyclopenta[c]pyrrol-2(1H)-yl)(tetrahydro-2H-pyran-4-yl)methanone. ((3aR,5s,6aS)-5-((7-Chlorothieno[2,3-d]pyridazin-4-yl)amino) hexahydrocyclopenta[c]pyrrol-2(1H)-yl)(tetrahydro-2H-pyran-4-yl)methanone (20 mg, 0.05 mmol,1 eq), 2,5-difluorophenylboronic acid (11.6 mg, 0.07 mmol, 1.5 eq), potassium carbonate (20.7 mg, 0.15 mmol, 3 eq), and BrettPhos-Pd-G³ (4.5 mg, 0.005 mmol, 0.1 eq) were combined and sealed in a vial and placed under and inert atmosphere. 5:1 1,4-dioxane/H₂O solution (1.25 ml, degassed) was added via syringe and reaction was heated under an inert atmosphere at 100° C. for 3 h. The reaction was then cooled, diluted in H₂O, extracted in DCM, and concentrated. The crude residue was purified by RP-HPLC (5-55% MeCN in 0.1% TFA aqueous solution over 6 min). Fractions containing product were basified with sat. NaHCO₃ solution, extracted in DCM, and concentrated to yield the title compound as a colorless oil (6.6 mg, 28%). ¹H-NMR (400 MHz, CDCl3) δ7.74 (d, J=5.4 Hz, 1H), 7.50-7.43 (m, 1H), 7.36 (d, J=5.5 Hz, 1H), 7.22-7.11 (m, 2H), 4.98-4.88 (m, 2H), 4.07-3.99 (m, 2H), 3.84-3.70 (m, 2H), 3.49-3.36 (m, 4H), 3.05-2.94 (m, 1H), 2.94-2.84 (m, 1H), 2.65-2.56 (m, 1H), 2.36-2.29 (m, 1H), 2.20-2.12 (m, 1H), 2.01-1.84 (m, 4H), 1.71-1.57 (m, 2H). ES-MS [M+H]⁺= 485.2.

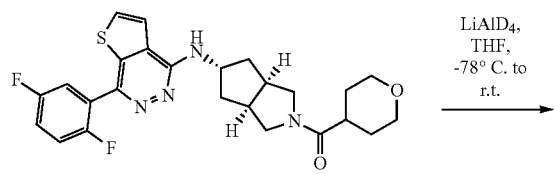

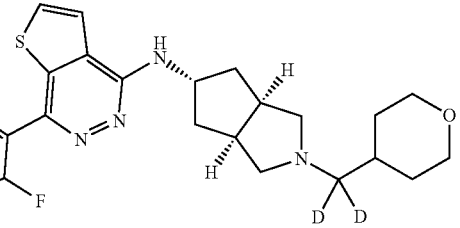

7-(2,5-Difluorophenyl)-N-((3aR,5s,6aS)-2-((tetrahydro-2H-pyran-4-yl) methyl-d2)octahydrocyclopenta[c]pyrrol-5-yl)thieno[2,3-d]pyridazin-4-amine. ((3aR,5s,6aS)-5-((7-(2, 5-Difluorophenyl)thieno[2,3-d]pyridazin-4-yl) amino) hexahydrocyclopenta[c]pyrrol-2(1H)-yl)(tetrahydro-2H-pyran-4-yl)methanone (6.6 mg, 0.014 mmol, 1 eq) in THF (0.6 mL) was cooled to −78° C. before the dropwise addition of lithium aluminum deuteride (3 mg, 0.08 mmol, 5.8 eq) in THF (0.4 mL). After 1 min, the reaction mixture was warmed to r.t. for 10 min. The reaction was quenched with the addition of H₂O (0.02 mL) followed by 1M NaOH (0.1 mL), after which time MgSO₄ was added for an additional 10 min. The reaction mixture was extracted in DCM and concentrated. The crude residue was purified by RP-HPLC (15-45% MeCN in 0.1% TFA aqueous solution over 4 min). Fractions containing product were basified with sat. NaHCO₃ solution, extracted in DCM, and concentrated to yield the title compound as a white solid (1.5 mg, 23%). ¹H-NMR (400 MHz, CDCl3) δ7.71 (d, J=5.4 Hz, 1H), 7.52-7.46 (m, 1H), 7.34 (d, J=5.5 Hz, 1H), 7.21-7.10 (m, 2H), 4.99-4.89 (m, 1H), 4.77 (d, J=7.1 Hz, 1H), 3.96 (dd, J=11.2, 3.9 Hz, 2H), 3.39 (td, J=12.2, 1.9 Hz, 2H), 2.82-2.71 (m, 4H), 2.26 (d, J=4.9 Hz, 2H), 2.07, (dd, J=6.8, 6.2 Hz, 2H), 1.79-1.65 (m, 5H) 1.35-1.26 (m, 2H). ES-MS [M+H]⁺= 473.2.

Example 6. 7-(4,4-Difluoropiperidin-1-yl)-N-((3aR,5s, 6aS)-2-((tetrahydro-2H-pyran-4-yl) methyl)octahydrocyclopenta[c]pyrrol-5-yl)thieno[2,3-d]pyridazin-4-amine.

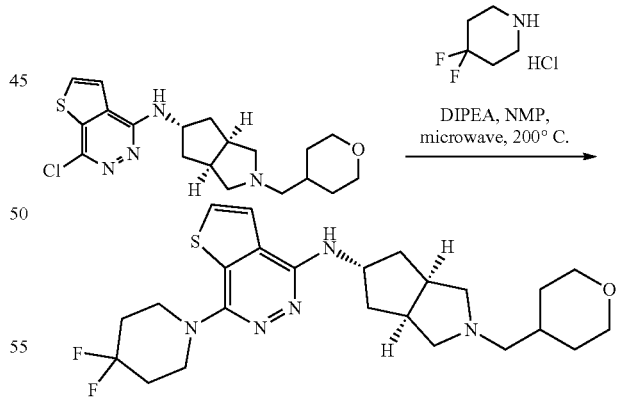

7-Chloro-N-((3aR,5s,6aS)-2-((tetrahydro-2H-pyran-4-yl) methyl)octahydrocyclopenta[c]pyrrol-5-yl)thieno[2,3-d] pyridazin-4-amine (13 mg, 0.003 mmol, 1 eq), 4,4-difluoropiperidine hydrochloride (37 mg, 0.23 mmol, 7.1 eq), and DIPEA (0.04 mL, 0.23 mmol, 7 eq) were sealed in a microwave vial, followed by the addition of NMP (0.65 mL). After 4 h at 200° C., the reaction mixture was purified directly by RP-HPLC (40-85% MeCN in 0.05% NH₄OH aqueous solution over 5 min). Fractions containing product were concentrated to yield the title compound as a tan oil (7.7 mg, 49%). ¹-H-NMR (400 MHz, CDCl3) δ7.64 (d, J=5.5 Hz, 1H), 7.27 (d, J=5.5 Hz, 1H), 4.80-4.71 (m, 1H), 4.40 (d, J=6.9 Hz, 1H), 3.95 (dd, J=11.7, 3.9 Hz, 2H), 3.65 (t, J=7.2 Hz, 4H), 3.37 (td, J=12.0, 1.8 Hz, 2H), 2.77-2.70 (m, 4H), 2.26-2.11 (m, 8H), 2.08 (dd, J=12.8, 6.4 Hz, 2H), 1.76-1.61 (m, 5H), 1.34-1.21 (m, 2H). ES-MS [M+H]⁺ =478.2.

Example 7. 4-(2,5-Difluorophenyl)-N-((3aR,5s,6aS)-2-((tetrahydro-2H-pyran-4-yl)methyl-d2) octahydrocyclopenta[c]pyrrol-5-yl)phthalazin-1-amine.

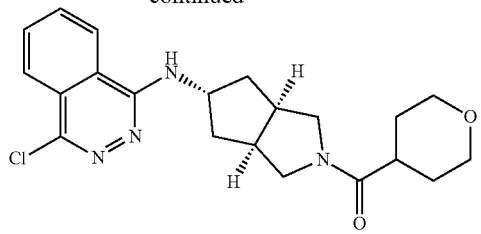

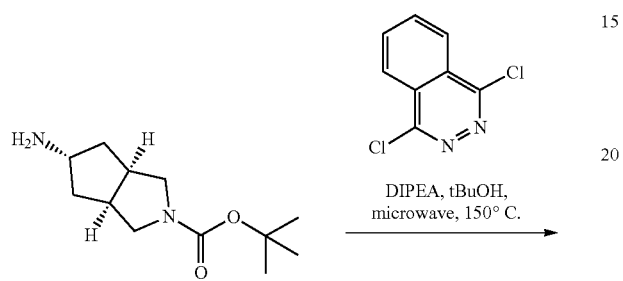

tert-Butyl (3aR,5s,6aS)-5-(4-chlorophthalazin-1-yl) amino)hexahydrocyclopenta[c]pyrrole-2(1H)-carboxylate. tert-Butyl (3aR,5s,6aS)-5-aminohexahydrocyclopenta[c] pyrrole-2(1H)-carboxylate (414 mg, 1.83 mmol, 1 eq) and 1,4-dichlorophthalazine (1.09 g, 5.49 mmol, 3 eq) were dissolved in tert-butanol (2.5 mL), and DIPEA (0.96 mL, 5.49 mmol, 3 eq) was added. The resulting solution was stirred for 2 h at 150° C. under microwave irradiation, after which time solvents were concentrated, and solids were removed by filtration. The filtrate was concentrated and purified by column chromatography (3-80% EtOAc in hexanes) to give the title compound as a white solid (417 mg, 59%). ES-MS [M+H]⁺=389.2.

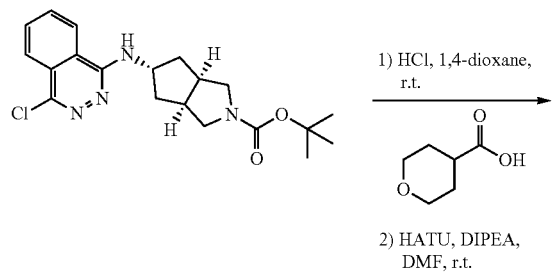

((3aR,5s,6aS)-5-(4-Chlorophthalazin-1-yl) amino)hexahydrocyclopenta[c]pyrrol-2(1H)-yl)(tetrahydro-2H-pyran-4-yl)methanone. tert-Butyl (3aR, 5s, 6aS)-5-((4-chlorophthalazin-1-yl)amino)hexahydrocyclopenta[c]pyrrole-2(1H)-carboxylate (415 mg, 1.07 mmol) was dissolved in 1,4-dioxane (5 mL) and 4M HCl in dioxanes solution (5 mL) was added dropwise. The resulting cloudy mixture was stirred at r.t. for 1 h, after which time solvents were concentrated under reduced pressure to give a white solid which was dried under vacuum and used without further purification (347 mg, 100%). ES-MS [M+H]⁺=289.4. To a solution of the hydrochloride salt (347 mg, 1.07 mmol, 1 eq) and tetrahydro-2H-pyran-4-carboxylic acid (153 mg, 1.17 mmol, 1.1 eq) in DMF (6 mL) was added DIPEA (0.56 mL, 3.20 mmol, 3 eq) followed by HATU (608 mg, 1.60 mmol, 1.5 eq). The resulting solution was stirred at r.t. for 30 min, after which time the reaction mixture was purified directly by RP-HPLC (7-47% MeCN in 0.05% NH₄OH aqueous solution over 20 min). Fractions containing product were concentrated to give the title compound as a white solid (336 mg, 79%). ES-MS [M+H]⁺=401.4.

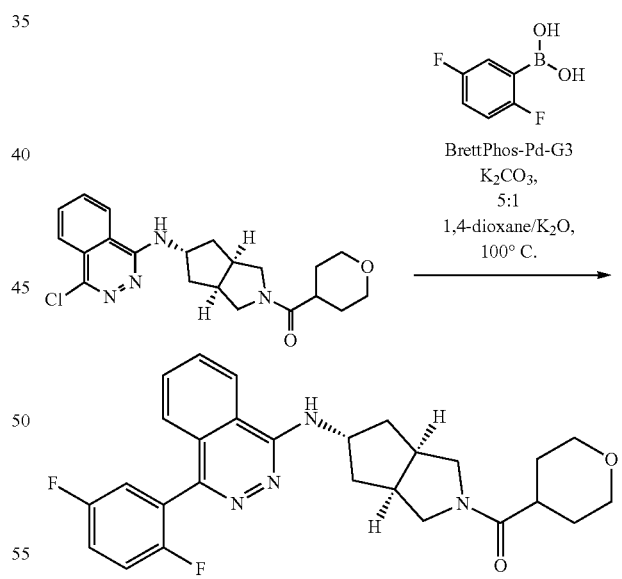

((3aR,5s,6aS)-5-((4-(2,5-Difluorophenyl)phthalazin-1-yl) amino)hexahydrocyclopenta[c]pyrrol-2(1H)-yl)(tetrahydro-2H-pyran-4-yl)methanone. ((3aR,5s,6aS)-5-((4-Chlorophthalazin-1-yl)amino)hexahydrocyclopenta[c]pyrrol-2(1H)-yl) (tetrahydro-2H-pyran-4-yl)methanone (30 mg, 0.075 mmol, 1 eq), 2,5-difluorophenylboronic acid (18 mg, 0.11 mmol, 1.5 eq), potassium carbonate (31 mg, 0.22 mmol, 3 eq) and BrettPhos-Pd-G³ (6.8 mg, 0.0075 mmol, 0.1 eq) were added to a vial, which was sealed and placed under an inert atmosphere. 5:1 1,4-dioxane/H₂O solution (1 mL, degassed) was added via syringe. The resulting mixture was stirred under an inert atmosphere at 100° C. for 1 h, after which time the reaction mixture was cooled to r.t. and diluted with DCM and H2O. The aqueous layer was extracted with DCM, and combined organic extracts were filtered through a phase separator and concentrated. The crude residue was purified by RP-HPLC (10-50% MeCN in 0.05% NH$_4$OH aqueous solution over 5 min). Fractions containing product were concentrated to give the title compound as a colorless oil (5.6 mg, 16%). ES-MS [M+H]$^+$= 479.4.

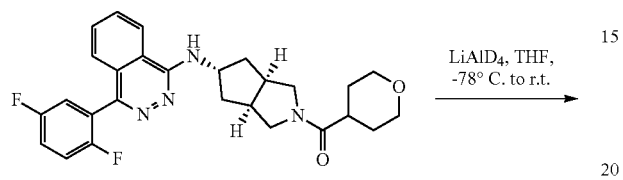

4-(2,5-Difluorophenyl)-N-((3aR,5s,6aS)-2-((tetrahydro-2H-pyran-4-yl) methyl-d2)octahydrocyclopenta[c]pyrrol-5-yl)phthalazin-1-amine. ((3aR,5s,6aS)-5-((4-(2,5-Difluorophenyl)phthalazin-1-yl)amino)hexahydrocyclopenta[c]pyrrol-2(1H)-yl)(tetrahydro-2H-pyran-4-yl)methanone (5.6 mg, 0.012 mmol, 1 eq) was dissolved in THF (0.25 mL) and cooled to −78° C. A solution of lithium aluminum deuteride (2.2 mg, 0.059 mmol, 5 eq) in THF (0.25 mL) was added dropwise. The resulting solution was stirred for 5 min at −78° C. and then warmed to r.t. After 30 min of stirring, another portion of lithium aluminum deuteride (5 eq) was added. The reaction was stirred for an additional 30 min, after which time it was quenched with the sequential addition of H$_2$O (20 µL) 1M NaOH solution (20 µL) and H$_2$O (50 µL). The reaction was stirred for 5 min, after which time MgSO$_4$ was added, followed by 5 mins of additional stirring. The reaction mixture was diluted with DCM, filtered through a phase separator and concentrated. The crude residue was purified by RP-HPLC (5-35% MeCN in 0.1% TFA aqueous solution over 5 min). Fractions containing product were basified with sat. NaHCO$_3$, and extracted with DCM. The combined organic extracts were concentrated to give the title compound as a white solid (3.3 mg, 60%). $^1$-NMR (400 MHz, CDCl3) δ7.93-7.76 (m, 3H), 7.66 (dd, J =8.0, 3.5 Hz, 1H), 7.38-7.33 (m, 1H), 7.17 (td, J =6.5, 1.7 Hz, 2H), 5.11-4.97 (m, 1H), 3.98 (dd, J=11.4, 4.0 Hz, 2H), 3.40 (td, J=11.9, 1.8 Hz, 2H), 3.22-3.00 (m, 2H), 2.55-2.35 (m, 2H), 2.23 (dd, J=12.2, 5.8 Hz, 2H), 2.00-1.50 (m, 7H), 1.44-1.29 (m, 2H). Note: NH signal not visible in spectra. ES-MS [M+H]$^+$=467.5.

Example 8. 4-(2,5-Difluorophenyl)-N-((3aR,5s,6aS)-2-((tetrahydro-2H-pyran-4-yl) methyl)octahydrocyclopenta[c] pyrrol-5-yl)-5,6,7,8-tetrahydrophthalazin-1-amine.

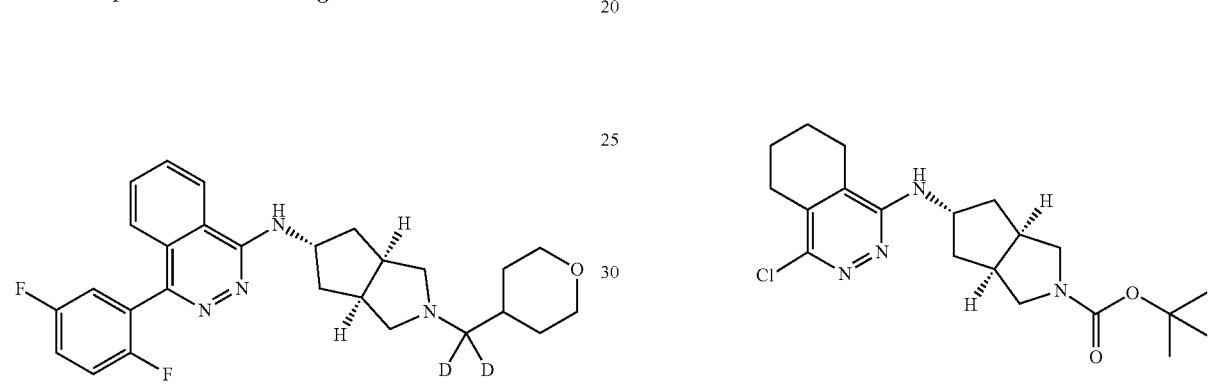

tert-Butyl (3aR,5s,6aS)-5-(4-chloro-5,6,7,8-tetrahydrophthalazin-1-yl) amino)hexahydrocyclopenta[c]pyrrole-2(1H)-carboxylate. To a solution of tert-butyl (3aR,5s,6aS)-5-aminohexahydrocyclopenta[c]pyrrole-2(1H)-carboxylate (300 mg, 1.33 mmol, 1 eq) and 1,4-dichloro-5,6,7,8-tetrahydrophthalazine (203 mg, 1.33 mmol, 1 eq) in tert-butanol (2 mL) and NMP (2 mL) was added DIPEA (0.69 mL, 4.0 mmol, 3 eq). The resulting solution was stirred under microwave irradiation at 150° C. for 4 h, after which time the reaction mixture was diluted with EtOAc and H$_2$O, and extracted with EtOAc. The combined organic extracts were dried over MgSO$_4$ and concentrated. The crude residue was purified by column chromatography (3-80% EtOAc in hexanes) to give the title compound as a yellow oil (135 mg total recovery, 26% (title compound is isolated as an inseparable mixture of desired product and Boc-deprotection/bis phthalazine addition product)). ES-MS [M+H]$^+$=393.2.

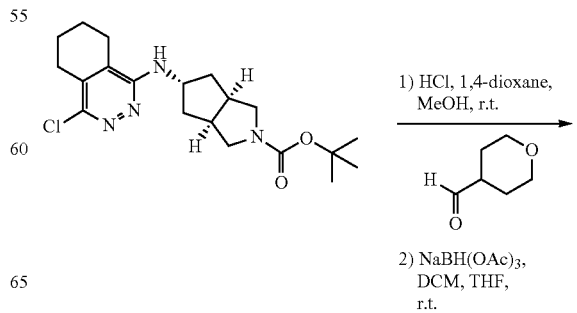

-continued

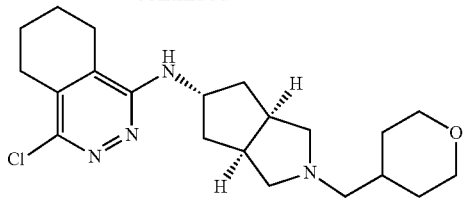

4-Chloro-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine. To a solution of tert-butyl (3aR,5s,6aS)-5-((4-chloro-5,6,7,8-tetrahydrophthalazin-1-yl)amino)hexahydrocyclopenta[c]pyrrole-2(1H)-carboxylate (135 mg, 0.35 mmol, 1 eq) in MeOH (1.7 ml) and 1,4-dioxane (5 ml) was added dropwise 4M HCl in dioxanes solution (1.3 mL). The resulting mixture was stirred at r.t. for 2 h after which time solvents were concentrated under reduced pressure. The crude residue was dried under vacuum and used without further purification (113 mg, 100%). ES-MS[M+H]$^+$=293.2. The resulting hydrochloride salt was taken up in DCM (2 mL) and THF (2 mL) and 4-oxanaldehyde was added (58.8 mg, 0.52 mmol, 1.5 eq) followed by the addition of sodium triacetoxyborohydride (146 mg, 0.69 mmol, 2 eq), and the reaction was stirred at r.t. overnight. The reaction mixture was quenched with sat. NaHCO$_3$, extracted in DCM and washed with brine and dried over MgSO$_4$. Solvents were filtered and concentrated. The crude residue was purified by RP-HPLC (5-45% MeCN in 0.05% NH$_4$OH aqueous solution over 10 min). Fractions containing product were concentrated to give the title compound as a colorless oil (44 mg, 33%). ES-MS [M+H]$^+$=391.2.

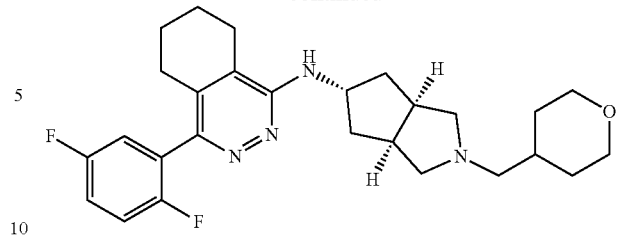

4-(2,5-Difluorophenyl)-N-((3aR,5s,6aS)-2-((tetrahydro-2H-pyran-4-yl) methyl)octahydrocyclopenta[c]pyrrol-5-yl)-5,6,7,8-tetrahydrophthalazin-1-amine. 4-Chloro-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine (15 mg, 0.038 mmol, 1 eq), 2,5-difluorophenylboronic acid (9.1 mg, 0.058 mmol, 1.5 eq), potassium carbonate (16.1 mg, 0.12 mmol, 3 eq), and BrettPhos-Pd-G$^3$ (3.5 mg, 0.004 mmol, 0.1 eq) were combined in a sealed vial which was placed under an inert atmosphere, followed by the addition of 5:1 1,4-dioxane/H$_2$O solution (0.65 mL, degassed) via syringe. The reaction was stirred at 100° C. for 2 h, after which time the reaction mixture was cooled to r.t and diluted with DCM and H$_2$O. The aqueous layer was extracted with DCM, and the organic extracts were filtered through a phase separator and concentrated. The crude residue was purified by RP-HPLC (45-90% MeCN in 0.05% NH$_4$OH aqueous solution over 5 min). Fractions containing product were concentrated to give the title compound as a colorless oil (6.2 mg, 35%). $^1$H-NMR (400 MHz, CDCl$_3$) δ7.19-7.15 (m, 1H), 7.07 (td, J=6.4, 1.7 Hz, 2H), 4.86-4.77 (m, 1H), 4.12 (d, J=6.6 Hz, 1H), 3.96 (dd, J=11.3, 3.6 Hz, 2H), 3.38 (td, J=12.0, 1.8 Hz, 2H), 3.01-2.76 (m, 2H), 2.50-2.21 (m, 8H), 2.11 (dd, J=12.4, 5.8 Hz, 2H), 1.93-1.87 (m, 2H), 1.84-1.61 (m, 9H), 1.36-1.24 (m, 2H). ES-MS [M+H]$^+$=469.2.

The compounds shown in Table 1 may be prepared similarly to the compounds described above, with appropriate starting materials.

TABLE 1

| Cpd. No. | Name | Structure | ES-MS [M + 1]$^+$ |
|---|---|---|---|
| 1 | 7-chloro-N-((3aR,5s,6aS)-2-((tetrahydro-2H-pyran-4-yl)methyl)octahydrocyclopenta[c]pyrrol-5-yl)thieno[2,3-d]pyridazin-4-amine | 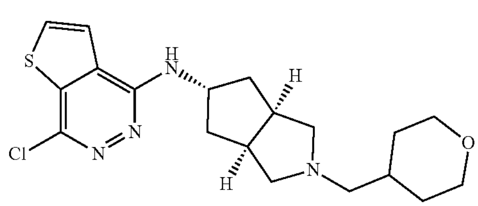 [SMILES: Clc1nnc(N[C@H]2C[C@@H]3CN(CC4CCOCC4)C[C@@H]3C2)c2ccsc12] | 393.4 |

TABLE 1-continued

| Cpd. No. | Name | Structure | ES-MS [M + 1]+ |
|---|---|---|---|
| 2 | 7-(2,5-difluorophenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 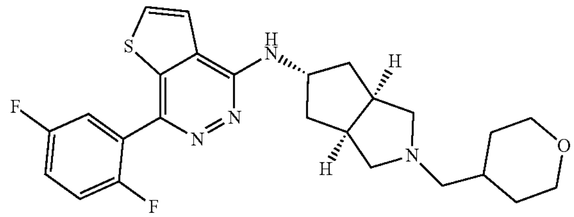 [SMILES: Fc1ccc(F)c(-c2nnc(N[C@H]3C[C@@H]4CN(CC5CCOCC5)C[C@@H]4C3)c3ccsc23)c1] | 471.4 |
| 3 | 7-(5-fluoro-2-methylphenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 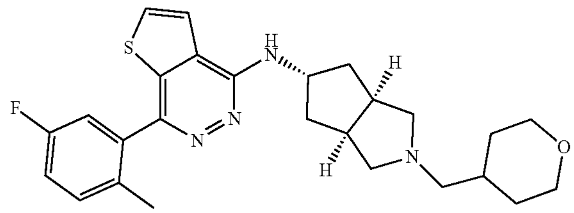 [SMILES: Cc1ccc(F)cc1-c1nnc(N[C@H]2C[C@@H]3CN(CC4CCOCC4)C[C@@H]3C2)c2ccsc12] | 467.4 |
| 4 | 7-(2,5-dimethylphenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 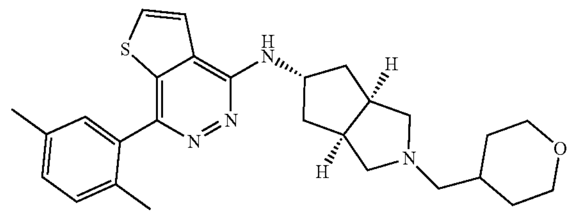 [SMILES: Cc1ccc(C)c(-c2nnc(N[C@H]3C[C@@H]4CN(CC5CCOCC5)C[C@@H]4C3)c3ccsc23)c1] | 463.5 |
| 5 | N-((3aR,5s,6aS)-2-((tetrahydro-2H-pyran-4-yl)methyl)octahydrocyclopenta[c]pyrrol-5-yl)-7-(o-tolyl)thieno[2,3-d]pyridazin-4-amine | 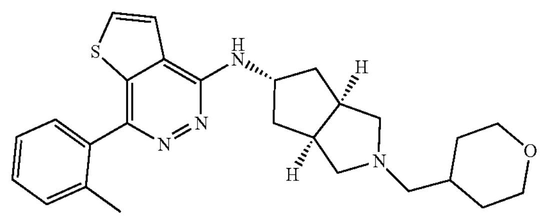 [SMILES: Cc1ccccc1-c1nnc(N[C@H]2C[C@@H]3CN(CC4CCOCC4)C[C@@H]3C2)c2ccsc12] | 449.4 |
| 6 | 7-(2-methoxyphenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 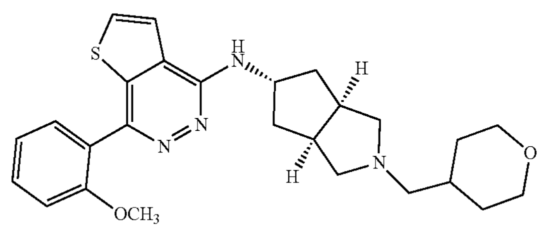 [SMILES: COc1ccccc1-c1nnc(N[C@H]2C[C@@H]3CN(CC4CCOCC4)C[C@@H]3C2)c2ccsc12] | 465.4 |
| 7 | 7-(2-fluorophenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 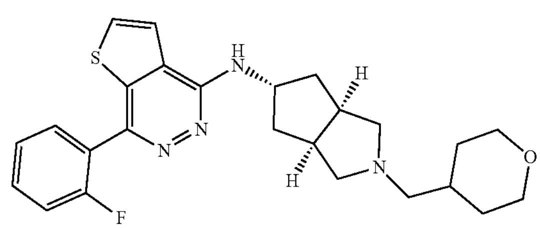 [SMILES: Fc1ccccc1-c1nnc(N[C@H]2C[C@@H]3CN(CC4CCOCC4)C[C@@H]3C2)c2ccsc12] | 453.4 |
| 8 | 7-phenyl-N-((3aR,5s,6aS)-2-((tetrahydro-2H-pyran-4-yl)methyl)octahydrocyclopenta[c]pyrrol-5-yl)thieno[2,3-d]pyridazin-4-amine | 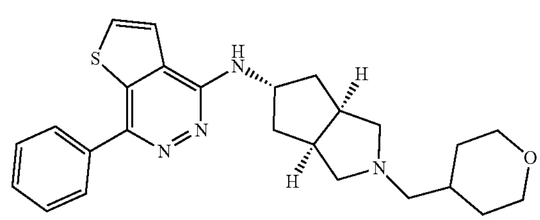 [SMILES: c1ccc(-c2nnc(N[C@H]3C[C@@H]4CN(CC5CCOCC5)C[C@@H]4C3)c3ccsc23)cc1] | 435.4 |

| Cpd. No. | Name | ES-MS [M + 1]+ |
|---|---|---|
| 9 | 7-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 489.2 |
| 10 | 4-(2,5-difluorophenyl)-N-((3aR,5s,6aS)-2-((tetrahydro-2H-pyran-4-yl)methyl)octahydrocyclopenta[c]pyrrol-5-yl)thieno[2,3-d]pyridazin-7-amine | 471.4 |
| 11 | 4-(5-fluoro-2-methylphenyl)-N-((3aR,5s,6aS)-2-((tetrahydro-2H-pyran-4-yl)methyl)octahydrocyclopenta[c]pyrrol-5-yl)thieno[2,3-d]pyridazin-7-amine | 467.4 |
| 12 | 4-chloro-N-((3aR,5s,6aS)-2-((tetrahydro-2H-pyran-4-yl)methyl)octahydrocyclopenta[c]pyrrol-5-yl)thieno[2,3-d]pyridazin-7-amine | 393.2 |
| 13 | 4-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-7-amine | 489.4 |
| 14 | 4-phenyl-N-((3aR,5s,6aS)-2-((tetrahydro-2H-pyran-4-yl)methyl)octahydrocyclopenta[c]pyrrol-5-yl)thieno[2,3-d]pyridazin-7-amine | 435.4 |
| 15 | 4-(2-fluorophenyl)-N-((3aR,5s,6aS)-2-((tetrahydro-2H-pyran-4-yl)methyl)octahydrocyclopenta[c]pyrrol-5-yl)thieno[2,3-d]pyridazin-7-amine | 453.4 |

TABLE 1-continued

| Cpd. No. | Name | Structure | ES-MS [M + 1]+ |
|---|---|---|---|
| 16 | N-((3aR,5s,6aS)-2-((tetrahydro-2H-pyran-4-yl)methyl)octahydrocyclopenta[c]pyrrol-5-yl)-7-(2,3,5-trifluorophenyl)thieno[2,3-d]pyridazin-4-amine | 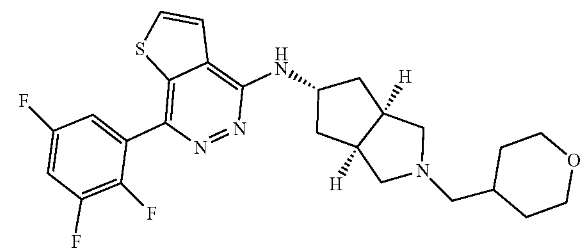 [SMILES: Fc1cc(F)c(F)c(-c2nnc(N[C@H]3C[C@@H]4CN(CC5CCOCC5)C[C@@H]4C3)c3ccsc23)c1] | 489.2 |
| 17 | 7-(2,4-dimethyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 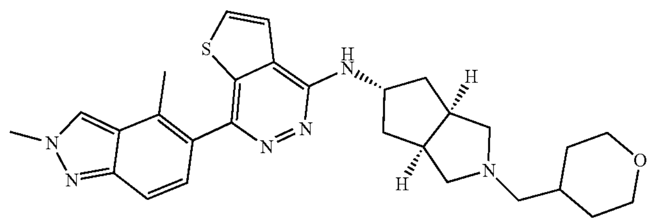 [SMILES: Cc1c(-c2nnc(N[C@H]3C[C@@H]4CN(CC5CCOCC5)C[C@@H]4C3)c3ccsc23)ccc2nn(C)cc12] | 503.2 |
| 18 | 7-(2,5-difluorophenyl)-N-((3aR,5s,6aS)-2-((tetrahydro-2H-pyran-4-yl)methyl-d2)octahydrocyclopenta[c]pyrrol-5-yl)thieno[2,3-d]pyridazin-4-amine | 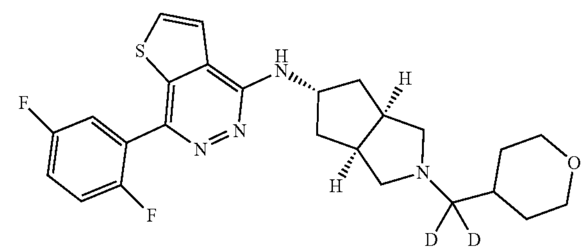 | 473.2 |
| 19 | 7-(5-fluoro-2-methylphenyl)-N-((3aR,5s,6aS)-2-((tetrahydro-2H-pyran-4-yl)methyl-d2)octahydrocyclopenta[c]pyrrol-5-yl)thieno[2,3-d]pyridazin-4-amine | 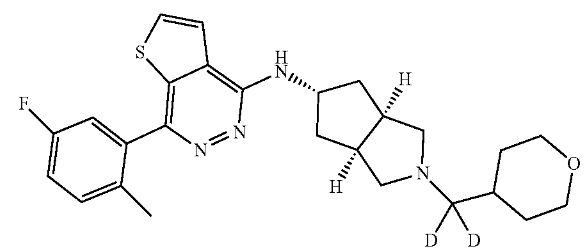 [SMILES: [2H]C([2H])(C1CCOCC1)N1C[C@H]2C[C@H](Nc3nnc(-c4cc(F)ccc4C)c4sccc34)C[C@H]2C1] | 469.2 |
| 20 | 7-(4,4-difluoropiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 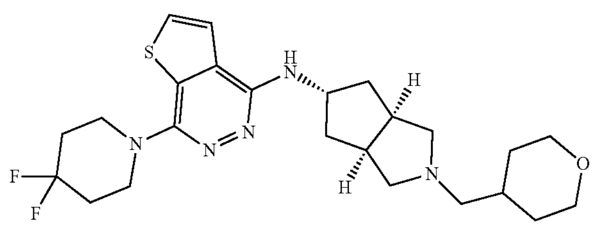 [SMILES: FC1(F)CCN(c2nnc(N[C@H]3C[C@@H]4CN(CC5CCOCC5)C[C@@H]4C3)c3ccsc23)CC1] | 478.2 |
| 21 | 7-((S)-3-methylpiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine | 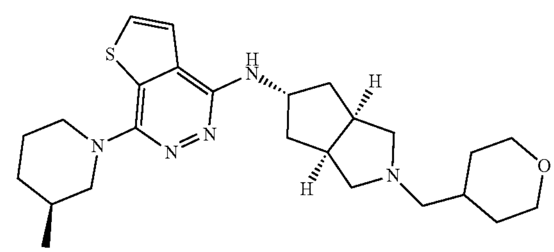 [SMILES: C[C@H]1CCCN(c2nnc(N[C@H]3C[C@@H]4CN(CC5CCOCC5)C[C@@H]4C3)c3ccsc23)C1] | 456.2 |

TABLE 1-continued

| Cpd. No. | Name | Structure | ES-MS [M + 1]+ |
|---|---|---|---|
| 22 | 4-(4,4-difluoropiperidin-1-yl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine | 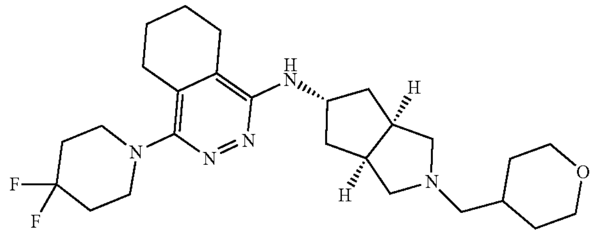 [SMILES: FC1(F)CCN(c2nnc(N[C@H]3C[C@@H]4CN(CC5CCOCC5)C[C@@H]4C3)c3c2CCCC3)CC1] | 476.5 |
| 23 | 4-(2,5-difluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine | 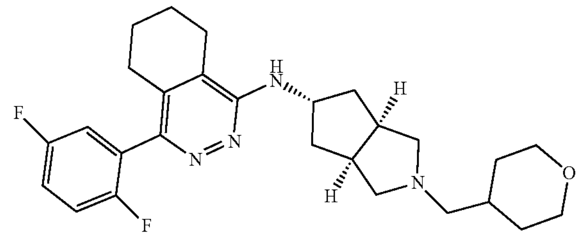 [SMILES: Fc1ccc(F)c(-c2nnc(N[C@H]3C[C@@H]4CN(CC5CCOCC5)C[C@@H]4C3)c3c2CCCC3)c1] | 469.2 |
| 24 | 4-(2-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine | 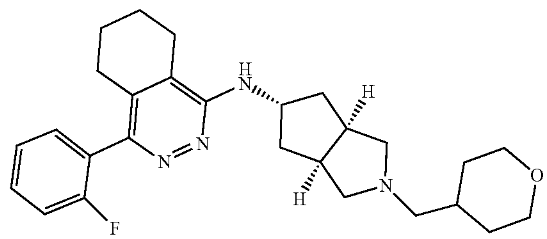 [SMILES: Fc1ccccc1-c1nnc(N[C@H]2C[C@@H]3CN(CC4CCOCC4)C[C@@H]3C2)c2c1CCCC2] | 451.2 |
| 25 | 4-(3-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine | 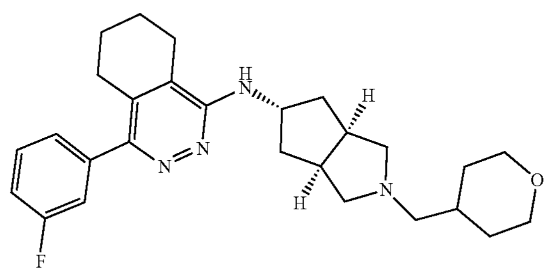 [SMILES: Fc1cccc(-c2nnc(N[C@H]3C[C@@H]4CN(CC5CCOCC5)C[C@@H]4C3)c3c2CCCC3)c1] | 451.4 |
| 26 | 4-(4-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine | 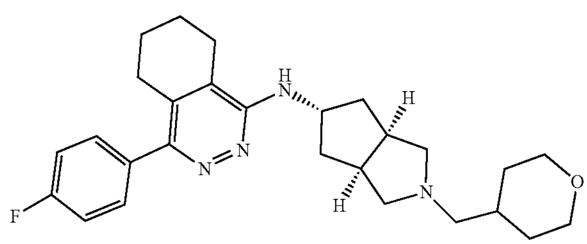 [SMILES: Fc1ccc(-c2nnc(N[C@H]3C[C@@H]4CN(CC5CCOCC5)C[C@@H]4C3)c3c2CCCC3)cc1] | 451.2 |
| 27 | 4-(2,5-difluorophenyl)-N-((3aR,5s,6aS)-2-((tetrahydro-2H-pyran-4-yl)methyl-d2)octahydrocyclopenta[c]pyrrol-5-yl)phthalazin-1-amine | 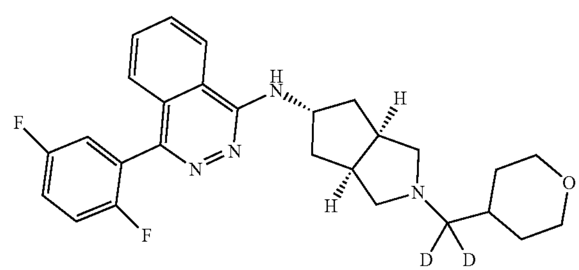 [SMILES: [2H]C([2H])(C1CCOCC1)N1C[C@H]2C[C@H](Nc3nnc(-c4cc(F)ccc4F)c4ccccc34)C[C@H]2C1] | 467.5 |

Biological Activity

A. Cell Lines Expressing Muscarinic Acetylcholine Receptors

Human or rat $M_4$ cDNA, along with the chimeric G protein $G_{qi5}$, were transfected into Chinese hamster ovary (CHO-K1) cells purchased from the American Type Culture Collection using Lipofectamine2000. $M_4/G_{qi5}$/CHO cells were grown in Ham's F-12 medium containing 10% heat-inactivated fetal bovine serum (FBS), 20 mM HEPES, 500 µg/mL 418 sulfate, and 200 µg/mL Hygromycin B.

B. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking 418 and hygromycin at 15,000 cells/20 µL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with assay buffer; the final volume was then aspirated to 20 µL. Next, 20 µL of a 2.3 µM stock of Fluo-4/acetoxymethyl ester (Invitrogen, Carlsbad, CA), prepared as a 2.3 mM stock in DMSO and mixed in a 1:1 ratio with 10% (w/v) Pluronic F-127 and diluted in assay buffer, was added to the wells and the cell plates were incubated for 50 min at 37° C. and 5% $CO_2$. Dye was removed by washing with the ELX 405 and the final volume was aspirated to 20 µL. Compound master plates were formatted in a 10 point concentration-response curve (CRC) format (1:3 dilutions) in 100% DMSO with a starting concentration of 10 or 1 mM using a BRAVO liquid handler (Agilent). Test compound CRCs were then transferred to daughter plates (240 nL) using the Echo acoustic plate reformatter (Labcyte, Sunnyvale, CA) and then diluted into assay buffer (40 µL) to a 2× stock using a Thermo Fisher Combi (Thermo Fisher Scientific, Waltham, MA).

Calcium flux was measured using the Functional Drug Screening System (FDSS) 6000 or 7000 (Hamamatsu Corporation, Tokyo, Japan) as an increase in the fluorescent static ratio. Compounds were applied to cells (20 µL, 2×) using the automated system of the FDSS at 2 seconds into the protocol and the data were collected at 1 Hz. At 143 s, 10 µL of an $EC_{20}$ concentration of the muscarinic receptor agonist acetylcholine was added (5×), followed by the addition of 12 µL of an $EC_{80}$ concentration of acetylcholine at the 268 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the ECK) acetylcholine response; for the purposes of the tables herein, an $IC_{50}$ (inhibitory concentration 50) was calculated as a concentration-dependent decrease of the response elicited by an ECK) concentration of acetylcholine. Concentration-response curves were generated using a four-parameter logistical equation in XLFit curve fitting software (IDBS, Bridgewater, NJ) for Excel (Microsoft, Redmond, WA) or Prism (GraphPad Software, Inc., San Diego, CA) or the Dotmatics software platform (Dotmatics, Bishop's Stortford, UK).

The above described assay was also operated in a second mode where an appropriate fixed concentration of the present compounds were added to the cells after establishment of a fluorescence baseline for about 3 seconds, and the response in cells was measured. 140 s later, a full concentration-response range consisting of increasing concentrations of agonist was added and the calcium response (maximum-local minima response) was measured. The $EC_{50}$ values for the agonist in the presence or absence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

C. Activity of Compounds in a mAChR $M_4$ Cell-Based Assay

Compounds were synthesized as described above. Activity ($IC_{50}$ and $E_{min}$) was determined in the mAChR $M_4$ cell-based functional assay as described above and the data are shown in Table 2.

TABLE 2

| | Human $M_4$ | |
|---|---|---|
| Cpd. No. | $IC_{50}$ (nM) | $E_{min}$ (%)* |
| 1 | 204 | 3 |
| 2 | 2.91 | 3 |
| 3 | 5.11 | 3 |
| 4 | 13.6 | 3 |
| 5 | 2.47 | 4 |
| 6 | 8080 | 20 |
| 7 | 7690 | 15 |
| 8 | 4.72 | 3 |
| 9 | 2.96 | 3 |
| 10 | 6.25 | 4 |
| 11 | 1.60 | 3 |
| 12 | 284 | 5 |
| 13 | 0.697 | 3 |
| 14 | 1.46 | 4 |
| 15 | 2.31 | 3 |
| 16 | 1.71 | 4 |
| 17 | 0.65 | 3 |
| 18 | 3.00 | 3 |
| 19 | 1.4 | 3 |
| 20 | 5.64 | 3 |
| 21 | 15.1 | 4 |
| 22 | 14.6 | 3 |
| 23 | 5.43 | 3 |
| 24 | 6.2 | 3 |
| 25 | 9.04 | 3 |
| 26 | 58.9 | 3 |
| 27 | 12.0 | 3 |

*% ACh maximum at 30 µM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I):

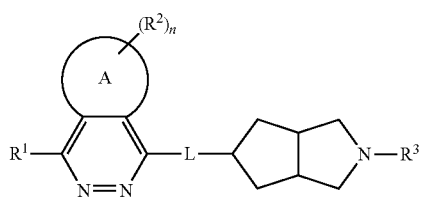

or a pharmaceutically acceptable salt thereof, wherein:
A is a 5- to 6-membered heteroarene, a 5- to 6-membered heterocycle, a 6-membered arene, or a 5- to 6-membered carbocycle, the heteroarene and heterocycle having 1, 2, or 3 heteroatoms independently selected from N, O, and S;
L is NR or O;
R is hydrogen, $C_{1-4}$alkyl, $C_{3-4}$cycloalkyl, or —$C_{1-3}$alkylene—$C_{3-4}$cycloalkyl;
$R^1$ is $G^1$, —$L'$—$G^1$, —$L'$—$C_{1-3}$alkylene—$G^1$—$C_{1-3}$alkylene—$G^1$, hydrogen, $C_{1-6}$alkyl, $C_{1-6}$haloalkyl, —$L'$—$C_{1-6}$alkyl, —$L'$—$C_{1-6}$haloalkyl, —C(O)NH$_2$, or halogen;
$L'$ is O, —N($R^{1a}$)—, S, S(O), SO$_2$, —C(O)—, or —N($R^{1a}$)C(O)—;
$G^1$ is a 6- to 12-membered aryl, a 5- to 12-membered heteroaryl, a 4- to 12-membered heterocyclyl, or a $C_{3-12}$carbocyclyl, wherein $G^1$ is optionally substituted with 1-5 substituents independently selected from the group consisting of halogen, cyano, $C_{1-4}$alkyl, $C_{1-4}$haloalkyl, —$OR^{10}$, —$N(R^{10})_2$, —$NR^{10}C(O)R^{10}$, —$CONR^{10}R^{10}$, —$NR^{10}SO_2R^{11}$, $C_{1-3}$alkylene—$OR^{10}$, $C_{3-6}$cycloalkyl, and —$C_{1-3}$alkylene—$C_{3-6}$cycloalkyl;
$R^{1a}$ is hydrogen, $C_{1-4}$alkyl, $C_{1-4}$haloalkyl, $C_{3-4}$cycloalkyl, or —$C_{1-3}$alkylene—$C_{3-4}$cycloalkyl;
$R^{10}$, at each occurrence, is independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two $R^{10}$, together with a nitrogen to which the two $R^{10}$ attach form a 4- to 6-membered heterocyclic ring optionally substituted with 1-4 substituents independently selected from the group consisting of halogen and $C_{1-4}$alkyl;
$R^{11}$ is $C_{1-4}$alkyl, $C_{1-4}$haloalkyl, $C_{3-4}$cycloalkyl, or —$C_{1-3}$alkylene—$C_{3-4}$cycloalkyl;
$R^2$, at each occurrence, is independently halogen, cyano, $C_{1-4}$alkyl, $C_{1-4}$haloalkyl, $C_{2-4}$alkenyl, $C_{3-6}$cycloalkyl, or —$C_{1-3}$alkylene—$C_{3-4}$cycloalkyl;
n is 0, 1, 2, 3, or 4;
$R^3$ is $G^2$, —$L^1$—$G^2$, —$L^2$—$G^2$, —$C_{2-6}$alkylene—$R^{3a}$, or $C_{3-7}$alkyl;
$L^1$ is $C_{1-3}$alkylene;
$L^2$ is 1,1-cyclopropylene;
$G^2$ is a 6- to 12-membered aryl, a 5- to 12-membered heteroaryl, a 4- to 12-membered heterocyclyl, or a $C_{3-12}$carbocyclyl optionally fused to a 6-membered arene, wherein $G^2$ is optionally substituted with 1-5 substituents independently selected from the group consisting of halogen, cyano, $C_{1-4}$alkyl, $C_{1-4}$haloalkyl, —$OR^{13}$, —$N(R^{13})_2$, —$C_{1-3}$alkylene—$OR^{13}$, or —$C_{1-3}$alkylene—$N(R^{13})_2$;
$R^{3a}$ is —$OR^{14}$ or —$N(R^{14})_2$; and
$R^{13}$ and $R^{14}$, at each occurrence, are independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two $R^{13}$ or two $R^{14}$, together with a nitrogen to which the two $R^{13}$ or two $R^{14}$ attach form a 4- to 6-membered heterocyclic ring optionally substituted with 1-4 substituents independently selected from the group consisting of halogen and $C_{1-4}$alkyl.

Clause 2. The compound of clause 1, or a pharmaceutically acceptable salt thereof, wherein A is the 5-membered heteroarene.

Clause 3. The compound of clause 2, or a pharmaceutically acceptable salt thereof, wherein the 5-membered heteroarene is a thiophene.

Clause 4. The compound of clause 1, or a pharmaceutically acceptable salt thereof, wherein A is the 6-membered arene.

Clause 5. The compound of clause 1, or a pharmaceutically acceptable salt thereof, wherein A is the 6-membered carbocycle and the 6-membered carbocycle is a 6-membered cycloalkane.

Clause 6. The compound of any of clauses 1-5, or a pharmaceutically acceptable salt thereof, wherein n is 0.

Clause 7. The compound of clause 1, of formula (I-A)

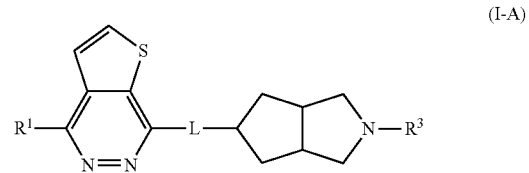

or a pharmaceutically acceptable salt thereof.

Clause 8. The compound of clause 1, of formula (I-B),

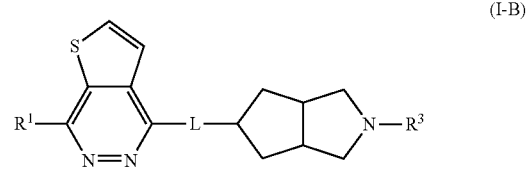

or a pharmaceutically acceptable salt thereof.

Clause 9. The compound of clause 1, of formula (I-C),

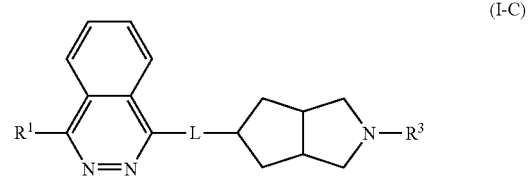

or a pharmaceutically acceptable salt thereof.

Clause 10. The compound of clause 1, of formula (I-D), (I-D)

or a pharmaceutically acceptable salt thereof.

Clause 11. The compound of any of clauses 1-10, or a pharmaceutically acceptable salt thereof, wherein $R^1$ is $G^1$.

Clause 12. The compound of clause 11, or a pharmaceutically acceptable salt thereof, wherein $G^1$ is the 6- to 12-membered aryl.

Clause 13. The compound of clause 12, or a pharmaceutically acceptable salt thereof, wherein the 6- to 12-membered aryl is a phenyl.

Clause 14. The compound of clause 11, or a pharmaceutically acceptable salt thereof, wherein $G^1$ is the 5- to 12-membered heteroaryl.

Clause 15. The compound of clause 14, or a pharmaceutically acceptable salt thereof, wherein the 5- to 12-membered heteroaryl is an indazolyl.

Clause 16. The compound of clause 11, or a pharmaceutically acceptable salt thereof, wherein $G^1$ is the 4- to 12-membered heterocyclyl.

Clause 17. The compound of clause 16, or a pharmaceutically acceptable salt thereof, wherein the 4- to 12-membered heterocyclyl is a 4- to 8-membered monocyclic heterocyclyl containing 1-2 heteroatoms independently selected from the group consisting of N and O.

Clause 18. The compound of clause 11, or a pharmaceutically acceptable salt thereof, wherein $G^1$ is phenyl, Clause 19. The compound of clause 11, or a pharmaceutically acceptable salt thereof, wherein $G^1$ is phenyl, Clause 20. The compound of any of clauses 1-19, or a pharmaceutically acceptable salt thereof, wherein $R^3$ is $-L^1-G^2$.

Clause 21. The compound of clause 20, or a pharmaceutically acceptable salt thereof, wherein $G^2$ is the 4- to 12-membered heterocyclyl.

Clause 22. The compound of clause 21, or a pharmaceutically acceptable salt thereof, wherein the 4- to 12-membered heterocyclyl is a 4- to 8-membered monocyclic heterocyclyl or a 7- to 12-membered spiro heterocyclyl, wherein the heterocyclyls contain one heteroatom selected from O and S.

Clause 23. The compound of clause 22, or a pharmaceutically acceptable salt thereof, wherein the 4- to 12-membered heterocyclyl is an oxetanyl, a tetrahydropyranyl, a tetrahydrothiopyranyl, a 2-oxaspiro[3.3]heptanyl, or a 3-oxaspiro[5.5]undecanyl.

Clause 24. The compound of clause 21, or a pharmaceutically acceptable salt thereof, wherein $G^2$ is Clause 25. The compound of clause 24, or a pharmaceutically acceptable salt thereof, wherein $G^2$ is

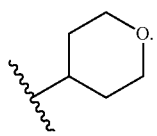 [SMILES: *C1CCOCC1]

Clause 26. The compound of any of clauses 1-25, or a pharmaceutically acceptable salt thereof, wherein L is NR.

Clause 27. The compound of clause 26, or a pharmaceutically acceptable salt thereof, wherein R is hydrogen.

Clause 28. The compound of any of clauses 1-27, or a pharmaceutically acceptable salt thereof, wherein $L^1$ is $CH_2$.

Clause 29. The compound of clause 1, wherein the compound is selected from the group consisting of:

7-chloro-N-((3aR,5s,6aS)-2-((tetrahydro-2H-pyran-4-yl)methyl)octahydrocyclopenta[c]pyrrol-5-yl) thieno[2,3-d]pyridazin-4-amine;

7-(2,5-difluorophenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-(5-fluoro-2-methylphenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-(2,5-dimethylphenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

N-((3aR,5s,6aS)-2-((tetrahydro-2H-pyran-4-yl)methyl)octahydrocyclopenta[c]pyrrol-5-yl)-'7-(o-tolyl) thieno[2,3-d]pyridazin-4-amine;

7-(2-methoxyphenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-(2-fluorophenyl)-N-((3aR,5s,6aS)-2-((tetrahydro-2H-pyran-4-yl) methyl)octahydrocyclopenta[c]pyrrol-5-yl)thieno[2,3-d]pyridazin-4-amine;

7-phenyl-N-((3aR,5s,6aS)-2-((tetrahydro-2H-pyran-4-yl)methyl)octahydrocyclopenta[c]pyrrol-5-yl)thieno[2,3-d]pyridazin-4-amine;

7-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

4-(2,5-difluorophenyl)-N-((3aR,5s,6aS)-2-((tetrahydro-2H-pyran-4-yl) methyl)octahydrocyclopenta[c]pyrrol-5-yl)thieno[2,3-d]pyridazin-7-amine;

4-(5-fluoro-2-methylphenyl)-N-((3aR,5s,6aS)-2-((tetrahydro-2H-pyran-4-yl) methyl)octahydrocyclopenta[c]pyrrol-5-yl)thieno[2,3-d]pyridazin-7-amine;

4-chloro-N-((3aR,5s,6aS)-2-((tetrahydro-2H-pyran-4-yl)methyl)octahydrocyclopenta[c]pyrrol-5-yl)thieno[2,3-d]pyridazin-7-amine;

4-(2-methyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-7-amine;

4-phenyl-N-((3aR,5s,6aS)-2-((tetrahydro-2H-pyran-4-yl)methyl)octahydrocyclopenta[c]pyrrol-5-yl)thieno[2,3-d]pyridazin-7-amine;

4-(2-fluorophenyl)-N-((3aR,5s,6aS)-2-((tetrahydro-2H-pyran-4-yl) methyl)octahydrocyclopenta[c]pyrrol-5-yl)thieno[2,3-d]pyridazin-7-amine;

N-((3aR,5s,6aS)-2-((tetrahydro-2H-pyran-4-yl)methyl)octahydrocyclopenta[c]pyrrol-5-yl)-'7-(2,3,5-trifluorophenyl)thieno[2,3-d]pyridazin-4-amine;

7-(2,4-dimethyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

7-(2,5-difluorophenyl)-N-((3aR,5s,6aS)-2-((tetrahydro-2H-pyran-4-yl) methyl-d2)octahydrocyclopenta[c]pyrrol-5-yl)thieno[2,3-d]pyridazin-4-amine;

7-(5-fluoro-2-methylphenyl)-N-((3aR,5s,6aS)-2-((tetrahydro-2H-pyran-4-yl) methyl-d2)octahydrocyclopenta[c]pyrrol-5-yl)thieno[2,3-d]pyridazin-4-amine;

7-(4,4-difluoropiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

7-((S)-3-methylpiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

4-(4,4-difluoropiperidin-1-yl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(2,5-difluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(2-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(3-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(4-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine; and 4-(2,5-difluorophenyl)-N-((3aR,5s,6aS)-2-((tetrahydro-2H-pyran-4-yl) methyl-d2)octahydrocyclopenta[c]pyrrol-5-yl)phthalazin-1-amine;

or a pharmaceutically acceptable salt thereof.

Clause 30. The compound of any of clauses 1-29, or a pharmaceutically acceptable salt thereof, wherein the compound is isotopically labeled.

Clause 31. A pharmaceutical composition comprising the compound of any of clauses 1-30, or a pharmaceutically acceptable salt thereof, and a pharmaceutically acceptable carrier.

Clause 32. A method for antagonizing mAChR $M_4$ in a subject, comprising administering to the subject a therapeutically effective amount of the compound of any of clauses 1-30, or a pharmaceutically acceptable salt thereof, or the pharmaceutical composition of clause 31.

Clause 33. A method for treating a disorder in a subject, wherein the subject would benefit from antagonism of mAChR $M_4$, comprising administering to the mammal a therapeutically effective amount of the compound of any of clauses 1-30, or a pharmaceutically acceptable salt thereof, or the pharmaceutical composition of clause 31.

Clause 34. The method of clause 33, wherein the disorder is a neurodegenerative disorder, a movement disorder, or a brain disorder.

Clause 35. The method of clause 34, wherein the disorder is a movement disorder.

Clause 36. The method of clause 34, wherein the disorder is selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

Clause 37. A method for treating motor symptoms in a subject, comprising administering to a subject in need thereof a therapeutically effective amount of the compound of any of clauses 1-30, or a pharmaceutically acceptable salt thereof, or the pharmaceutical composition of clause 31.

Clause 38. The method of clause 37, wherein the subject has a disorder selected from Parkinson's disease, drug-induced Parkinsonism, dystonia, Tourette's syndrome, dyskinesias, schizophrenia, cognitive deficits associated with schizophrenia, excessive daytime sleepiness, attention deficit hyperactivity disorder (ADHD), Huntington's disease, chorea, cerebral palsy, and progressive supranuclear palsy.

Clause 39. A compound of any of clauses 1-30, or a pharmaceutically acceptable salt thereof, or the pharmaceutical composition of clause 31, for use in the treatment of a neurodegenerative disorder, a movement disorder, or a brain disorder.

Clause 40. The use of a compound of any of clauses 1-30, or a pharmaceutically acceptable salt thereof, or the pharmaceutical composition of clause 31, for the preparation of a medicament for the treatment of a neurodegenerative disorder, a movement disorder, or a brain disorder.

The invention claimed is:
1. A compound of formula (I):

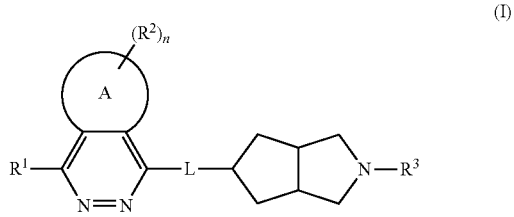

(I)

or a pharmaceutically acceptable salt thereof, wherein:
A is a 5- to 6-membered heteroarene, a 5- to 6-membered heterocycle, a 6-membered arene, or a 5- to 6-membered carbocycle, the heteroarene and heterocycle having 1, 2, or 3 heteroatoms independently selected from N, O, and S;
L is NR or O;
R is hydrogen, $C_{1-4}$alkyl, $C_{3-4}$cycloalkyl, or —$C_{1-3}$alkylene—$C_{3-4}$cycloalkyl;
$R^1$ is $G^1$, —L'—$G^1$, —L'—$C_{1-3}$alkylene—$G^1$, —$C_{1-3}$alkylene—$G^1$, hydrogen, $C_{1-6}$alkyl, $C_{1-6}$haloalkyl, —L'—$C_{1-6}$alkyl, —L'—$C_{1-6}$haloalkyl, —C(O)NH$_2$, or halogen;
L' is O, —N($R^{1a}$)—, S, S(O), SO$_2$, —C(O)—, or —N($R^{1a}$)C(O)—;
$G^1$ is a 5- to 12-membered heteroaryl, a 6- to 12-membered aryl, a 4- to 12-membered heterocyclyl, or a $C_{3-12}$carbocyclyl, wherein $G^1$ is optionally substituted with 1-5 substituents independently selected from the group consisting of halogen, cyano, $C_{1-4}$alkyl, $C_{1-4}$haloalkyl, —$OR^{10}$, —$N(R^{10})_2$, —$NR^{10}C(O)R^{10}$, —$CONR^{10}R^{10}$, —$NR^{10}SO_2R^{11}$, —$C_{1-3}$alkylene—$OR^{10}$, $C_{3-6}$cycloalkyl, and —$C_{1-3}$alkylene—$C_{3-6}$cycloalkyl;
$R^{1a}$ is hydrogen, $C_{1-4}$alkyl, $C_{1-4}$haloalkyl, $C_{3-4}$cycloalkyl, or —$C_{1-3}$alkylene—$C_{3-4}$cycloalkyl;
$R^{10}$, at each occurrence, is independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two $R^{10}$ together with a nitrogen to which the two $R^{10}$ attach form a 4-to 6-membered heterocyclic ring optionally substituted with 1-4 substituents independently selected from the group consisting of halogen and $C_{1-4}$alkyl;
$R^{11}$ is $C_{1-4}$alkyl, $C_{1-4}$haloalkyl, $C_{3-4}$cycloalkyl, or —$C_{1-3}$alkylene—$C_{3-4}$cycloalkyl;
$R^2$, at each occurrence, is independently halogen, cyano, $C_{1-4}$alkyl, $C_{1-4}$haloalkyl, $C_{2-4}$alkenyl, $C_{3-6}$cycloalkyl, or —$C_{1-3}$alkylene—$C_{3-4}$cycloalkyl;
n is 0, 1, 2, 3, or 4;
$R^3$ is —$L^1$—$G^2$, $G^2$, —$L^2$—$G^2$, —$L^2L^1$—$G^2$, —$C_{2-6}$alkylene—$R^{3a}$, or $C_{3-7}$alkyl;
$L^1$ is $C_{1-3}$alkylene;
$L^2$ is 1,1-cyclopropylene;
$G^2$ is a 4-to 12-membered heterocyclyl a 6-to 12-membered aryl, a 5-to 12-membered heteroaryl, or a $C_{3-12}$carbocyclyl optionally fused to a 6-membered arene, wherein $G^2$ is optionally substituted with 1-5 substituents independently selected from the group consisting of halogen, cyano, $C_{1-4}$alkyl, $C_{1-4}$haloalkyl, —$OR^{13}$, —$N(R^{13})_2$, —$C_{1-3}$alkylene—$OR^{13}$ or —$C_{1-3}$alkylene—$N(R^{13})_2$;
$R^{3a}$ is —$OR^{14}$ or —$N(R^{14})_2$; and
$R^{13}$ and $R^{14}$, at each occurrence, are independently hydrogen, $C_{1-4}$alkyl, $C_{1-4}$haloalkyl, $C_{3-4}$cycloalkyl, or —$C_{1-3}$alkylene—$C_{3-4}$cycloalkyl, wherein alternatively two $R^{13}$ or two $R^{14}$, together with a nitrogen to which the two $R^{13}$ or two $R^{14}$ attach form a 4-to 6-membered heterocyclic ring optionally substituted with 1-4 substituents independently selected from the group consisting of halogen and $C_{1-4}$alkyl.

2. The compound of claim 1, or a pharmaceutically acceptable salt thereof, wherein A is a thiophene.

3. The compound of claim 1, of formula (I-A), (I-B), (I-C), or (I-D),

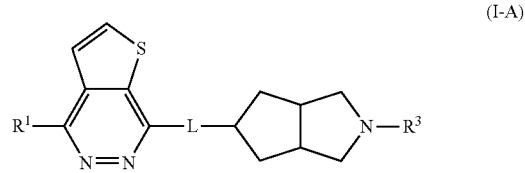

(I-A)

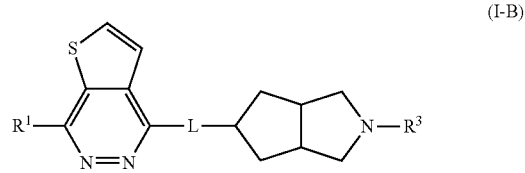

(I-B)

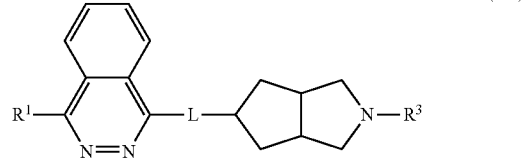

(I-C)

-continued

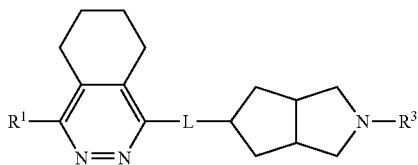
(I-D)

or a pharmaceutically acceptable salt thereof.

4. The compound of claim 1, or a pharmaceutically acceptable salt thereof, wherein $G^1$ is the 5-to 12-membered heteroaryl.

5. The compound of claim 1, or a pharmaceutically acceptable salt thereof, wherein $G^1$ is the 6-to 12-membered aryl.

6. The compound of claim 1, or a pharmaceutically acceptable salt thereof, wherein $G^1$ is the 4-to 12-membered heterocyclyl.

7. The compound of claim 1, or a pharmaceutically acceptable salt thereof, wherein $G^1$ is

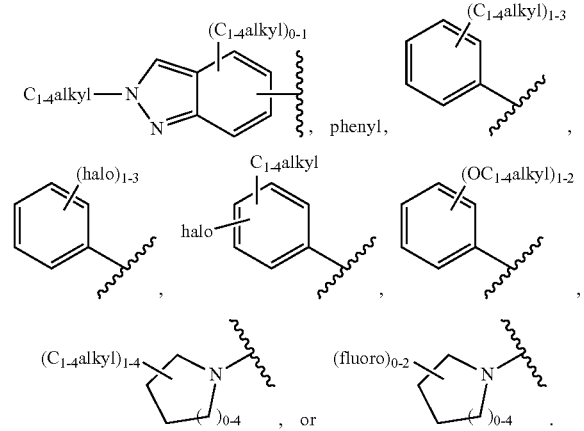

8. The compound of claim 1, or a pharmaceutically acceptable salt thereof, wherein $L^1$ is $CH_2$.

9. The compound of claim 1, or a pharmaceutically acceptable salt thereof, wherein $G^2$ is the 4-to 12-membered heterocyclyl.

10. The compound of claim 9, or a pharmaceutically acceptable salt thereof, wherein $G^2$ is a tetrahydropyranyl, an oxetanyl, a tetrahydrothiopyranyl, a 2-oxaspiro[3.3]heptanyl, or a 3-oxaspiro[5.5]undecanyl.

11. The compound of claim 10, or a pharmaceutically acceptable salt thereof, wherein $G^2$ is

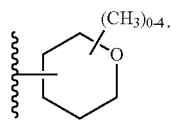

12. The compound of claim 11, or a pharmaceutically acceptable salt thereof, wherein $G^2$ is

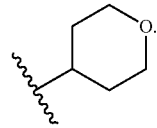

13. The compound of claim 1, or a pharmaceutically acceptable salt thereof, wherein R is hydrogen.

14. The compound of claim 1 selected from the group consisting of
7-chloro-N-((3aR,5s,6aS)-2-((tetrahydro-2H-pyran-4-yl) methyl)octahydrocyclopenta[c]pyrrol-5-yl)thieno[2,3-d]pyridazin-4-amine;
7-(2,5-difluorophenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine;
7-(5-fluoro-2-methylphenyl)-N-((3aR,5s,6aS)-2-((tetrahydro-2H-pyran-4-yl)methyl)octahydrocyclopenta[c] pyrrol-5-yl)thieno[2,3-d]pyridazin-4-amine;
7-(2,5-dimethylphenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine;
N-((3aR,5s,6aS)-2-((tetrahydro-2H-pyran-4-yl methyl) octahydrocyclopenta[c]pyrrol-5-yl)-7-(o-tolyl)thieno [2,3-d]pyridazin-4-amine;
7-(2-methoxyphenyl)-N-((3aR,5s,6aS)-2-((tetrahydro-2H-pyran-4-yl)methyl)octahydrocyclopenta[c]pyrrol-5-yl)thieno[2,3-d]pyridazin-4-amine;
7-(2-fluorophenyl)-N-((3aR,5s,6aS)-2-((tetrahydro-2H-pyran-4-yl)methyl)octahydrocyclopenta[c]pyrrol-5-yl) thieno[2,3-d]pyridazin-4-amine;
7-phenyl-N-((3aR,5s,6aS)-2-((tetrahydro-2H-pyran-4-yl) methyl)octahydrocyclopenta[c]pyrrol-5-yl)thieno[2,3-d]pyridazin-4-amine;
7-(2-methyl-2H-indazol-5-yl)-N-((3aR,5s,6aS)-2-((tetrahydro-2H-pyran-4-yl)methyl)octahydrocyclopenta[c] pyrrol-5-yl)thieno[2,3-d]pyridazin-4-amine;
4-(2,5-difluorophenyl)-N-((3aR,5s,6aS)-2-((tetrahydro-2H-pyran-4-yl)methyl)octahydrocyclopenta[c]pyrrol-5-yl)thieno[2,3-d]pyridazin-7-amine;
4-(5-fluoro-2-methylphenyl)-N-((3aR,5s,6aS)-2-((tetrahydro-2H-pyran-4-yl)methyl)octahydrocyclopenta[c] pyrrol-5-yl)thieno[2,3-d]pyridazin-7-amine;
4-chloro-N-((3aR,5s,6aS)-2-((tetrahydro-2H-pyran-4-yl) methyl)octahydrocyclopenta[c]pyrrol-5-yl)thieno[2,3-d]pyridazin-7-amine;
4-(2-methyl-2H-indazol-5-yl)-N-((3aR,5s,6aS)-2-((tetrahydro-2H-pyran-4-yl)methyl)octahydrocyclopenta[c] pyrrol-5-yl)thieno[2,3-d]pyridazin-7-amine;
4-phenyl-N-((3aR,5s,6aS)-2-((tetrahydro-2H-pyran-4-yl) methyl)octahydrocyclopenta[c]pyrrol-5-yl)thieno[2,3-d]pyridazin-7-amine;
4-(2-fluorophenyl)-N-((3aR,5s,6aS)-2-((tetrahydro-2H-pyran-4-yl)methyl)octahydrocyclopenta[c]pyrrol-5-yl) thieno[2,3-d]pyridazin-7-amine;
N-((3aR,5s,6aS)-2-((tetrahydro-2H-pyran-4-yl)methyl) octahydrocyclopenta[c]pyrrol-5-yl)-7-(2,3,5-trifluorophenyl)thieno[2,3-d]pyridazin-4-amine;
7-(2,4-dimethyl-2H-indazol-5-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;
7-(2,5-difluorophenyl)-N-((3aR,5s,6aS)-2-((tetrahydro-2H-pyran-4-yl)methyl-d2)octahydrocyclopenta[c]pyrrol-5-yl)thieno[2,3-d]pyridazin-4-amine;

7-(5-fluoro-2-methylphenyl)-N-((3aR,5s,6aS)-2-((tetrahydro-2H-pyran-4-yl)methyl-d2)octahydrocyclopenta[c]pyrrol-5-yl)thieno[2,3-d]pyridazin-4-amine;

7-(4,4-difluoropiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine; and 7-((S)-3-methylpiperidin-1-yl)-N-((3aR,5s,6aS)-2-((tetrahydro-2H-pyran-4-yl)methyl)octahydrocyclopenta[c]pyrrol-5-yl)thieno[2,3-d]pyridazin-4-amine;

4-(4,4-difluoropiperidin-1-yl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(2,5-difluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(2-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(3-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine;

4-(4-fluorophenyl)-N-((3aR,5s,6aS)-2-((tetrahydro-2H-pyran-4-yl)methyl)octahydrocyclopenta[c]pyrrol-5-yl)-5,6,7,8-tetrahydrophthalazin-1-amine; and 4-(2,5-difluorophenyl)-N-((3aR,5s,6aS)-2-((tetrahydro-2H-pyran-4-yl)methyl-d2)octahydrocyclopenta[c]pyrrol-5-yl)phthalazin-1-amine;

or a pharmaceutically acceptable salt thereof.

15. A pharmaceutical composition comprising the compound of claim 1, or a pharmaceutically acceptable salt thereof, and a pharmaceutically acceptable carrier.

16. A method for antagonizing mAChR $M_4$ in a subject, comprising administering to the subject a therapeutically effective amount of the compound of claim 1, or a pharmaceutically acceptable salt thereof.

17. A method for treating a disorder in a subject, wherein the subject would benefit from antagonism of mAChR $M_4$, comprising administering to the subject a therapeutically effective amount of the compound of claim 1, or a pharmaceutically acceptable salt thereof.

18. The method of claim 17, wherein the disorder is a neurodegenerative disorder, a movement disorder, or a brain disorder.

19. The method of claim 18, wherein the disorder is a movement disorder.

20. A method for treating motor symptoms in a subject, comprising administering to a subject in need thereof a therapeutically effective amount of the compound of claim 1, or a pharmaceutically acceptable salt thereof.

* * * * *